United States Patent
Rush et al.

(10) Patent No.: US 8,652,141 B2
(45) Date of Patent: Feb. 18, 2014

(54) METHODS AND DEVICES FOR TREATING HALLUX VALGUS

(75) Inventors: Shannon M. Rush, Pleasanton, CA (US); Peter T. Keith, Lanesboro, MN (US); Paul M. Sand, Redwood City, CA (US); John Avi Roop, Palo Alto, CA (US); Jason W. Lettmann, Menlo Park, CA (US); Joshua Baltzell, Palo Alto, CA (US)

(73) Assignee: Tarsus Medical Inc., Mountain View, CA (US)

( * ) Notice: Subject to any disclaimer, the term of this patent is extended or adjusted under 35 U.S.C. 154(b) by 752 days.

(21) Appl. No.: 12/691,646

(22) Filed: Jan. 21, 2010

(65) Prior Publication Data

US 2011/0178557 A1     Jul. 21, 2011

(51) Int. Cl.
*A61F 2/46* (2006.01)
*A61B 17/58* (2006.01)
*A61F 2/00* (2006.01)
*A61B 17/60* (2006.01)

(52) U.S. Cl.
USPC ........................................ 606/86 R; 606/105

(58) Field of Classification Search
USPC ........... 606/86 R, 90, 99, 103–105, 148, 232, 606/228; 623/21.15
See application file for complete search history.

(56) References Cited

U.S. PATENT DOCUMENTS

| | | | |
|---|---|---|---|
| 2,291,413 A | 7/1942 | Siebrandt |
| 3,867,929 A | 2/1975 | Joyner et al. |
| 3,880,155 A | 4/1975 | Rosoff |
| 3,987,559 A | 10/1976 | Roberts |
| 4,069,824 A | 1/1978 | Weinstock |
| 4,213,208 A | 7/1980 | Marne |
| 4,240,214 A | 12/1980 | Sigle et al. |
| 4,244,359 A | 1/1981 | Dieterich |
| 4,255,875 A | 3/1981 | Gilkerson |
| 4,263,902 A | 4/1981 | Dieterich |
| 4,266,553 A | 5/1981 | Faiella |
| 4,300,294 A | 11/1981 | Riecken |
| 4,314,412 A | 2/1982 | Anderson et al. |
| 4,317,293 A | 3/1982 | Sigle et al. |
| 4,393,876 A | 7/1983 | Dieterich |
| 4,409,974 A | 10/1983 | Freedland |
| 4,414,964 A | 11/1983 | Farino et al. |
| 4,439,934 A | 4/1984 | Brown |

(Continued)

FOREIGN PATENT DOCUMENTS

| | | | |
|---|---|---|---|
| EP | 60353 A1 | 9/1982 |
| EP | 284922 A2 | 10/1988 |

(Continued)

OTHER PUBLICATIONS

Mini TightRope™ for Hallux Valgus Correction and Lisfranc Ligament Repair Surgical Technique, Anthrex, copyright 2007, 6 pp.

(Continued)

*Primary Examiner* — Andrew Yang
*Assistant Examiner* — Diana S Jones
(74) *Attorney, Agent, or Firm* — Peter Materna; Eva Tan

(57) ABSTRACT

The various embodiments disclosed herein relate to implantable devices for the treatment of structural bone and joint deformity, including hallux valgus. More specifically, the various embodiments include systems, devices, and methods for implantation of a flexible or tension band for treating such deformity.

2 Claims, 16 Drawing Sheets

(56) References Cited

U.S. PATENT DOCUMENTS

| | | |
|---|---|---|
| 4,510,699 A | 4/1985 | Nakamura et al. |
| 4,583,303 A | 4/1986 | Laiacona et al. |
| 4,597,195 A | 7/1986 | Dananberg |
| 4,603,698 A | 8/1986 | Guttmann |
| 4,604,997 A | 8/1986 | De Bastiani et al. |
| 4,608,988 A | 9/1986 | Dananberg |
| 4,632,103 A | 12/1986 | Fabricant et al. |
| 4,644,940 A | 2/1987 | Nakamura |
| 4,676,801 A | 6/1987 | Lundeen |
| 4,726,127 A | 2/1988 | Barouk |
| 4,729,369 A | 3/1988 | Cook |
| 4,738,255 A | 4/1988 | Goble et al. |
| RE32,698 E | 6/1988 | Brown |
| 4,813,162 A | 3/1989 | Harris |
| 4,819,644 A | 4/1989 | Cherniak |
| 4,841,647 A | 6/1989 | Turucz |
| 4,842,931 A | 6/1989 | Zook |
| 4,852,556 A | 8/1989 | Groiso |
| 4,856,505 A | 8/1989 | Shaffer et al. |
| 4,876,758 A | 10/1989 | Rolloff et al. |
| 4,901,453 A | 2/1990 | Gaynor |
| 4,930,504 A | 6/1990 | Diamantopoulos et al. |
| 4,940,046 A | 7/1990 | Jacoby |
| 4,969,277 A | 11/1990 | Williams |
| 4,976,712 A | 12/1990 | VanderSlik |
| 5,005,575 A | 4/1991 | Geri |
| 5,012,596 A | 5/1991 | Schiller |
| 5,035,069 A | 7/1991 | Minden |
| 5,092,347 A | 3/1992 | Shaffer et al. |
| 5,094,226 A | 3/1992 | Medcalf et al. |
| 5,098,421 A | 3/1992 | Zook |
| 5,138,777 A | 8/1992 | Darby |
| 5,167,665 A | 12/1992 | McKinney |
| 5,174,052 A | 12/1992 | Schoenhaus et al. |
| 5,250,049 A | 10/1993 | Michael |
| D341,424 S | 11/1993 | Lurie |
| 5,272,139 A | 12/1993 | Cary, Jr. |
| 5,306,301 A | 4/1994 | Graf et al. |
| 5,350,383 A | 9/1994 | Schmieding et al. |
| RE34,753 E | 10/1994 | Groiso |
| 5,497,789 A | 3/1996 | Zook |
| 5,529,075 A | 6/1996 | Clark |
| 5,537,764 A | 7/1996 | Prahl |
| 5,539,020 A | 7/1996 | Bracken et al. |
| 5,571,139 A | 11/1996 | Jenkins, Jr. |
| 5,601,565 A | 2/1997 | Huebner |
| 5,607,756 A | 3/1997 | Yamauchi et al. |
| 5,611,801 A | 3/1997 | Songer |
| 5,617,651 A | 4/1997 | Prahl |
| 5,640,779 A | 6/1997 | Rolloff et al. |
| 5,645,588 A | 7/1997 | Graf et al. |
| 5,664,112 A | 9/1997 | Thal |
| 5,665,060 A | 9/1997 | Fabricant |
| 5,685,834 A | 11/1997 | Barth |
| H1706 H | 1/1998 | Mason |
| 5,725,585 A | 3/1998 | Zobel |
| 5,728,136 A | 3/1998 | Thal |
| 5,788,697 A | 8/1998 | Kilpela et al. |
| 5,792,093 A | 8/1998 | Tanaka |
| 5,797,913 A | 8/1998 | Dambreville et al. |
| 5,802,737 A | 9/1998 | Beppu |
| 5,810,822 A | 9/1998 | Mortier |
| 5,813,903 A | 9/1998 | Amano et al. |
| 5,843,085 A | 12/1998 | Graser |
| 5,853,293 A | 12/1998 | Weber et al. |
| 5,919,194 A | 7/1999 | Anderson |
| 5,921,986 A | 7/1999 | Bonutti |
| 5,962,011 A | 10/1999 | DeVillez et al. |
| 6,001,101 A | 12/1999 | Augagneur et al. |
| 6,068,648 A | 5/2000 | Cole et al. |
| 6,091,000 A | 7/2000 | Haynes |
| 6,093,163 A | 7/2000 | Chong et al. |
| 6,203,545 B1 | 3/2001 | Stoffella |
| 6,238,357 B1 | 5/2001 | Kawaguchi et al. |
| D443,694 S | 6/2001 | Ford |
| 6,248,109 B1 | 6/2001 | Stoffella |
| 6,248,788 B1 | 6/2001 | Robbins et al. |
| 6,264,677 B1 | 7/2001 | Simon et al. |
| 6,283,973 B1 | 9/2001 | Hubbard et al. |
| 6,315,749 B1 | 11/2001 | Sunayama |
| 6,318,373 B1 | 11/2001 | Kasahara |
| 6,319,270 B1 | 11/2001 | Grafton et al. |
| 6,348,053 B1 | 2/2002 | Cachia |
| 6,367,087 B1 | 4/2002 | Spillman et al. |
| 6,391,031 B1 | 5/2002 | Toomey |
| 6,406,234 B2 | 6/2002 | Frigg |
| 6,424,864 B1 | 7/2002 | Matsuura |
| 6,447,783 B1 | 9/2002 | Yayon |
| 6,478,761 B2 | 11/2002 | Bracamonte-Sommer |
| 6,481,120 B1 | 11/2002 | Xia et al. |
| 6,514,222 B2 | 2/2003 | Cook |
| 6,547,792 B1 | 4/2003 | Tsuji et al. |
| 6,547,800 B2 | 4/2003 | Foerster et al. |
| 6,569,188 B2 | 5/2003 | Grafton et al. |
| 6,583,114 B2 | 6/2003 | Vickery |
| 6,604,301 B1 | 8/2003 | Manoli, II et al. |
| 6,616,665 B2 | 9/2003 | Grafton et al. |
| 6,629,943 B1 | 10/2003 | Schroder |
| 6,643,956 B2 | 11/2003 | Mawusi et al. |
| 6,684,532 B2 | 2/2004 | Greene et al. |
| 6,689,136 B2 | 2/2004 | Stoffella |
| 6,716,234 B2 | 4/2004 | Grafton et al. |
| 6,800,063 B2 | 10/2004 | Iwata |
| 6,862,481 B1 | 3/2005 | Demian |
| 6,874,258 B2 | 4/2005 | Clough et al. |
| 6,887,243 B2 | 5/2005 | Culbert |
| 6,887,259 B2 | 5/2005 | Lizardi |
| 6,889,088 B2 | 5/2005 | Demian |
| 6,890,333 B2 | 5/2005 | von Hoffmann et al. |
| 6,902,799 B2 | 6/2005 | Chikamori |
| 6,908,465 B2 | 6/2005 | von Hoffmann et al. |
| 6,909,513 B1 | 6/2005 | Fujita et al. |
| 6,910,287 B2 | 6/2005 | Truelsen |
| 6,942,668 B2 | 9/2005 | Padget et al. |
| 6,964,645 B1 | 11/2005 | Smits |
| 6,991,636 B2 | 1/2006 | Rose |
| 7,008,428 B2 | 3/2006 | Cachia et al. |
| 7,013,583 B2 | 3/2006 | Greene et al. |
| 7,055,268 B2 | 6/2006 | Ha |
| 7,056,885 B1 | 6/2006 | Jeffers et al. |
| 7,062,866 B2 | 6/2006 | Bussler |
| 7,070,601 B2 | 7/2006 | Culbert et al. |
| 7,097,647 B2 | 8/2006 | Segler |
| 7,141,545 B2 | 11/2006 | Pike et al. |
| 7,175,667 B2 | 2/2007 | Saunders et al. |
| 7,192,411 B2 | 3/2007 | Gobet et al. |
| 7,217,853 B2 | 5/2007 | Kulichikhin et al. |
| 7,253,266 B2 | 8/2007 | Shimkets et al. |
| 7,263,788 B2 | 9/2007 | Johnson |
| 7,266,910 B2 | 9/2007 | Ingimundarson |
| 7,270,644 B2 | 9/2007 | Ingimundarson |
| 7,276,244 B2 | 10/2007 | Radovic |
| 7,287,293 B2 | 10/2007 | Cook et al. |
| 7,291,175 B1 | 11/2007 | Gordon |
| 7,291,483 B2 | 11/2007 | Shimkets et al. |
| 7,325,323 B2 | 2/2008 | Katsu et al. |
| 7,326,211 B2 | 2/2008 | Padget et al. |
| 7,383,089 B2 | 6/2008 | Demian |
| 7,392,605 B2 | 7/2008 | Hatfield et al. |
| 7,396,338 B2 | 7/2008 | Huber et al. |
| 7,485,135 B2 | 2/2009 | Steiger et al. |
| 7,493,810 B2 | 2/2009 | Walczyk et al. |
| 7,513,880 B2 | 4/2009 | Ingimundarson et al. |
| 7,572,258 B2 | 8/2009 | Stiernborg |
| 7,625,395 B2 | 12/2009 | Muckter |
| 7,875,058 B2 | 1/2011 | Holmes, Jr. |
| 8,277,459 B2 * | 10/2012 | Sand et al. ............ 606/96 |
| 2001/0027583 A1 | 10/2001 | Rothbart |
| 2001/0034956 A1 | 11/2001 | Mawusi et al. |
| 2002/0007134 A1 | 1/2002 | Bracamonte-Sommer |
| 2002/0022862 A1 | 2/2002 | Grafton et al. |
| 2002/0032466 A1 | 3/2002 | Grafton et al. |
| 2002/0056209 A1 | 5/2002 | Clough et al. |
| 2002/0058036 A1 | 5/2002 | Jeffers et al. |

(56) References Cited

U.S. PATENT DOCUMENTS

| | | |
|---|---|---|
| 2002/0062140 A1 | 5/2002 | Demian |
| 2002/0077281 A1 | 6/2002 | Vickery |
| 2002/0138026 A1 | 9/2002 | Cook |
| 2002/0162250 A1 | 11/2002 | Campbell et al. |
| 2002/0193309 A1 | 12/2002 | Yayon |
| 2003/0005601 A1 | 1/2003 | Kasahara |
| 2003/0023268 A1 | 1/2003 | Lizardi |
| 2003/0040750 A1 | 2/2003 | Stoffella |
| 2003/0045881 A1 | 3/2003 | Barouk et al. |
| 2003/0093920 A1 | 5/2003 | Greene et al. |
| 2003/0105193 A1 | 6/2003 | Wang |
| 2003/0134792 A1 | 7/2003 | Pike et al. |
| 2003/0148692 A1 | 8/2003 | Chikamori |
| 2003/0152637 A1 | 8/2003 | Chasin et al. |
| 2003/0172553 A1 | 9/2003 | Truelsen |
| 2003/0186433 A1 | 10/2003 | Shimkets et al. |
| 2003/0187372 A1 | 10/2003 | Iwata |
| 2003/0225356 A1 | 12/2003 | Kulichikhin et al. |
| 2004/0019308 A1 | 1/2004 | Chow |
| 2004/0031169 A1 | 2/2004 | Jensen et al. |
| 2004/0039319 A1 | 2/2004 | Calatayud Carral |
| 2004/0045194 A1 | 3/2004 | Kumai |
| 2004/0093746 A1 | 5/2004 | Varsallona |
| 2004/0103561 A1 | 6/2004 | Campbell et al. |
| 2004/0107604 A1 | 6/2004 | Ha |
| 2004/0123495 A1 | 7/2004 | Greene et al. |
| 2004/0127907 A1 | 7/2004 | Dakin et al. |
| 2004/0156931 A1 | 8/2004 | Burch et al. |
| 2004/0161481 A1 | 8/2004 | Burch et al. |
| 2004/0168329 A1 | 9/2004 | Ishimaru |
| 2004/0168353 A1 | 9/2004 | Bussler |
| 2004/0186182 A1 | 9/2004 | Burch et al. |
| 2004/0191338 A1 | 9/2004 | Burch et al. |
| 2004/0194348 A1 | 10/2004 | Campbell et al. |
| 2004/0194352 A1 | 10/2004 | Campbell et al. |
| 2004/0210234 A1 | 10/2004 | Coillard et al. |
| 2004/0243197 A1 | 12/2004 | Demian |
| 2005/0019436 A1 | 1/2005 | Burch et al. |
| 2005/0020690 A1 | 1/2005 | Burch et al. |
| 2005/0043734 A1 | 2/2005 | Kay |
| 2005/0054959 A1 | 3/2005 | Ingimundarson |
| 2005/0054962 A1 | 3/2005 | Bradshaw |
| 2005/0055849 A1 | 3/2005 | Ha |
| 2005/0058734 A1 | 3/2005 | Burch et al. |
| 2005/0059873 A1 | 3/2005 | Glozman et al. |
| 2005/0060910 A1 | 3/2005 | Kaneda et al. |
| 2005/0061332 A1 | 3/2005 | Greenawalt et al. |
| 2005/0063971 A1 | 3/2005 | Jeffers et al. |
| 2005/0070909 A1 | 3/2005 | Egger et al. |
| 2005/0076536 A1 | 4/2005 | Hatfield et al. |
| 2005/0115116 A1 | 6/2005 | Pedersen et al. |
| 2005/0123567 A1 | 6/2005 | First |
| 2005/0158382 A1 | 7/2005 | Cruz et al. |
| 2005/0177084 A1 | 8/2005 | Green et al. |
| 2005/0187071 A1 | 8/2005 | Yamashita et al. |
| 2005/0197711 A1 | 9/2005 | Cachia |
| 2005/0202047 A1 | 9/2005 | Radovic |
| 2005/0208540 A1 | 9/2005 | Shimkets et al. |
| 2005/0228389 A1 | 10/2005 | Stiernborg |
| 2005/0229430 A1 | 10/2005 | Takaba |
| 2005/0229433 A1 | 10/2005 | Cachia |
| 2005/0241187 A1 | 11/2005 | Johnson |
| 2005/0251081 A1 | 11/2005 | McClanahan et al. |
| 2006/0002954 A1 | 1/2006 | Tabata et al. |
| 2006/0015102 A1 | 1/2006 | Toullec et al. |
| 2006/0030854 A1 | 2/2006 | Haines |
| 2006/0058796 A1 | 3/2006 | Hartdegen et al. |
| 2006/0064048 A1 | 3/2006 | Stano |
| 2006/0074434 A1 | 4/2006 | Wenstrom et al. |
| 2006/0079558 A1 | 4/2006 | Aberg et al. |
| 2006/0079559 A1 | 4/2006 | Aberg et al. |
| 2006/0081553 A1 | 4/2006 | Patterson et al. |
| 2006/0148903 A1 | 7/2006 | Burch et al. |
| 2006/0155233 A1 | 7/2006 | Huber et al. |
| 2006/0161090 A1 | 7/2006 | Lee |
| 2006/0162464 A1 | 7/2006 | Hayashi et al. |
| 2006/0178702 A1 | 8/2006 | Pierce et al. |
| 2006/0189914 A1 | 8/2006 | Slavitt |
| 2006/0201011 A1 | 9/2006 | Katsu et al. |
| 2006/0240105 A1 | 10/2006 | Devane et al. |
| 2006/0241066 A1 | 10/2006 | Tomita et al. |
| 2006/0241607 A1 | 10/2006 | Myerson et al. |
| 2006/0241608 A1 | 10/2006 | Myerson et al. |
| 2006/0247566 A1 | 11/2006 | Gobet et al. |
| 2006/0251721 A1 | 11/2006 | Cruz et al. |
| 2006/0258588 A1 | 11/2006 | Pike et al. |
| 2006/0264961 A1 | 11/2006 | Murray-Brown |
| 2006/0269628 A1 | 11/2006 | Burch et al. |
| 2006/0271077 A1 | 11/2006 | Graser |
| 2006/0276737 A1 | 12/2006 | Rose |
| 2006/0282231 A1 | 12/2006 | Kurashina et al. |
| 2007/0010818 A1 | 1/2007 | Stone et al. |
| 2007/0016205 A1 | 1/2007 | Beutter et al. |
| 2007/0016275 A1 | 1/2007 | Ferdinand |
| 2007/0033750 A1 | 2/2007 | Cook et al. |
| 2007/0036876 A1 | 2/2007 | Burch et al. |
| 2007/0051020 A1 | 3/2007 | Tajima et al. |
| 2007/0051376 A1 | 3/2007 | Kulichikhin et al. |
| 2007/0074334 A1 | 4/2007 | Steel |
| 2007/0074426 A1 | 4/2007 | Dorsey |
| 2007/0078518 A1 | 4/2007 | Lavi |
| 2007/0088341 A1 | 4/2007 | Skiba et al. |
| 2007/0094896 A1 | 5/2007 | Hatfield et al. |
| 2007/0128226 A1 | 6/2007 | Radovic |
| 2007/0131798 A1 | 6/2007 | Katsukawa et al. |
| 2007/0141020 A1 | 6/2007 | Barritault et al. |
| 2007/0197948 A1 | 8/2007 | Ingimundarson et al. |
| 2007/0204487 A1 | 9/2007 | Clough |
| 2007/0213296 A1 | 9/2007 | Zhang |
| 2007/0213308 A1 | 9/2007 | Lessem et al. |
| 2007/0214681 A1 | 9/2007 | Dezfouli |
| 2007/0225217 A1 | 9/2007 | Chappell et al. |
| 2007/0225703 A1 | 9/2007 | Schmitz et al. |
| 2007/0260252 A1 | 11/2007 | Schmitz et al. |
| 2007/0265296 A1 | 11/2007 | Dalton et al. |
| 2007/0265634 A1 | 11/2007 | Weinstein |
| 2007/0281906 A1 | 12/2007 | Dalton et al. |
| 2007/0282342 A1 | 12/2007 | Niederberger et al. |
| 2007/0299382 A1 | 12/2007 | Millet |
| 2008/0008777 A1 | 1/2008 | Radovic |
| 2008/0010856 A1 | 1/2008 | Hakkala |
| 2008/0014272 A1 | 1/2008 | Skolnick et al. |
| 2008/0023012 A1 | 1/2008 | Dineen et al. |
| 2008/0027119 A1 | 1/2008 | Lippa et al. |
| 2008/0041169 A1 | 2/2008 | Walczyk et al. |
| 2008/0057068 A1 | 3/2008 | Dalton et al. |
| 2008/0065224 A1 | 3/2008 | Reigstad et al. |
| 2008/0076829 A1 | 3/2008 | Dalton et al. |
| 2008/0078628 A1 | 4/2008 | Christen |
| 2008/0081834 A1 | 4/2008 | Lippa et al. |
| 2008/0086139 A1 | 4/2008 | Bourke et al. |
| 2008/0086909 A1 | 4/2008 | Raspini |
| 2008/0086913 A1 | 4/2008 | Nawachi et al. |
| 2008/0102121 A1 | 5/2008 | Devane et al. |
| 2008/0113025 A1 | 5/2008 | Devane et al. |
| 2008/0139641 A1 | 6/2008 | Meyer |
| 2008/0141565 A1 | 6/2008 | Rini et al. |
| 2008/0147084 A1 | 6/2008 | Bleich et al. |
| 2008/0153780 A1 | 6/2008 | Meyer |
| 2008/0155731 A1 | 7/2008 | Kasahara |
| 2008/0200989 A1 | 8/2008 | Cachia |
| 2008/0208252 A1* | 8/2008 | Holmes ........................ 606/232 |
| 2008/0216593 A1 | 9/2008 | Jacobsen et al. |
| 2008/0217816 A1 | 9/2008 | Hemmi et al. |
| 2008/0221697 A1 | 9/2008 | Graser |
| 2008/0229482 A1 | 9/2008 | Millet |
| 2008/0242646 A1 | 10/2008 | Lessem et al. |
| 2008/0248282 A1 | 10/2008 | Martin et al. |
| 2008/0260791 A1 | 10/2008 | Burch et al. |
| 2008/0262091 A1 | 10/2008 | Burch et al. |
| 2008/0263900 A1 | 10/2008 | Determe et al. |
| 2008/0280975 A1 | 11/2008 | Badul |
| 2008/0282580 A1 | 11/2008 | Ji-Woog |
| 2008/0287406 A1 | 11/2008 | Lessem |

(56) References Cited

U.S. PATENT DOCUMENTS

| | | |
|---|---|---|
| 2008/0287866 A1 | 11/2008 | Heller |
| 2008/0288019 A1 | 11/2008 | Heller |
| 2008/0294170 A1 | 11/2008 | O'Brien |
| 2008/0301977 A1 | 12/2008 | Roberts et al. |
| 2009/0005358 A1 | 1/2009 | Lessem |
| 2009/0012180 A1 | 1/2009 | Lange et al. |
| 2009/0036893 A1 | 2/2009 | Kartalian et al. |
| 2009/0043318 A1 | 2/2009 | Michel et al. |
| 2009/0054527 A1 | 2/2009 | Burch et al. |
| 2009/0062253 A1 | 3/2009 | Gahman et al. |
| 2009/0062359 A1 | 3/2009 | Burch et al. |
| 2009/0082466 A1 | 3/2009 | Babul |
| 2009/0082773 A1 | 3/2009 | Haines |
| 2009/0082874 A1 | 3/2009 | Cachia |
| 2009/0111792 A1 | 4/2009 | Burch et al. |
| 2009/0113759 A1 | 5/2009 | Heid |
| 2009/0117167 A1 | 5/2009 | Burch et al. |
| 2009/0118242 A1 | 5/2009 | Burch et al. |
| 2009/0133289 A1 | 5/2009 | Cantoni |
| 2009/0156614 A1 | 6/2009 | Dalton et al. |
| 2009/0157194 A1 | 6/2009 | Shikinami |
| 2009/0181098 A1 | 7/2009 | Garrett et al. |
| 2009/0192222 A1 | 7/2009 | Yao et al. |
| 2009/0198287 A1 | 8/2009 | Chiu |
| 2009/0209536 A1 | 8/2009 | Gahman et al. |
| 2009/0210010 A1 | 8/2009 | Strnad et al. |
| 2009/0215809 A1 | 8/2009 | Yao et al. |
| 2009/0216334 A1 | 8/2009 | Leibel |
| 2009/0222047 A1 | 9/2009 | Graham |
| 2009/0228049 A1 | 9/2009 | Park |
| 2009/0287246 A1 | 11/2009 | Cauldwell et al. |
| 2009/0291975 A1 | 11/2009 | Stern et al. |
| 2009/0292022 A1 | 11/2009 | Kowalski et al. |
| 2009/0292023 A1 | 11/2009 | Kowalski et al. |
| 2009/0306723 A1 | 12/2009 | Anapliotis et al. |
| 2010/0036430 A1 | 2/2010 | Hartdegen et al. |
| 2010/0152752 A1* | 6/2010 | Denove et al. ............... 606/148 |
| 2010/0211071 A1* | 8/2010 | Lettmann et al. ............. 606/60 |
| 2011/0077656 A1 | 3/2011 | Sand et al. |
| 2011/0118780 A1 | 5/2011 | Holmes, Jr. |
| 2011/0224729 A1 | 9/2011 | Baker et al. |
| 2011/0301648 A1 | 12/2011 | Lofthouse et al. |
| 2012/0016426 A1* | 1/2012 | Robinson ..................... 606/328 |
| 2012/0071935 A1* | 3/2012 | Keith et al. .................. 606/328 |

FOREIGN PATENT DOCUMENTS

| | | | |
|---|---|---|---|
| EP | 40782 A2 | 7/1992 |
| EP | 491983 A1 | 7/1992 |
| EP | 557409 A1 | 9/1993 |
| EP | 649447 A1 | 4/1995 |
| EP | 679377 A2 | 11/1995 |
| EP | 757545 A1 | 2/1997 |
| EP | 796603 A1 | 9/1997 |
| EP | 991404 A1 | 4/2000 |
| EP | 1044618 A1 | 10/2000 |
| EP | 1056364 A1 | 12/2000 |
| EP | 1113768 A1 | 7/2001 |
| EP | 891160 B1 | 10/2001 |
| EP | 679377 B1 | 8/2002 |
| EP | 1287787 A1 | 3/2003 |
| EP | 995364 B1 | 6/2003 |
| EP | 1307116 B1 | 5/2005 |
| EP | 1531741 A1 | 5/2005 |
| EP | 1618806 A1 | 1/2006 |
| EP | 1691830 A1 | 8/2006 |
| EP | 1715888 A2 | 11/2006 |
| EP | 1464281 B1 | 12/2006 |
| EP | 1446028 B1 | 1/2007 |
| EP | 1772123 A1 | 4/2007 |
| EP | 1792577 A1 | 6/2007 |
| EP | 1800555 A1 | 6/2007 |
| EP | 1806062 A1 | 7/2007 |
| EP | 1513561 B1 | 9/2007 |
| EP | 1836981 A2 | 9/2007 |
| EP | 1885309 A2 | 2/2008 |
| EP | 1913831 A1 | 4/2008 |
| EP | 1927322 A1 | 6/2008 |
| EP | 1587506 B1 | 7/2008 |
| EP | 1952776 A1 | 8/2008 |
| FR | 2893496 A1 | 5/2007 |
| FR | 2916954 A1 | 12/2008 |
| GB | 2023404 A | 1/1980 |
| GB | 2228202 A | 8/1990 |
| GB | 2269753 A | 2/1994 |
| GB | 2337446 A | 11/1999 |
| GB | 2425961 A | 11/2006 |
| JP | 2071704 A | 3/1990 |
| JP | 2295572 A | 12/1990 |
| JP | 3188849 A | 8/1991 |
| JP | 4108401 A | 4/1992 |
| JP | 4129550 A | 4/1992 |
| JP | 5329005 A | 12/1993 |
| JP | 6054702 A | 3/1994 |
| JP | 6054872 A | 3/1994 |
| JP | 6062906 A | 3/1994 |
| JP | 6105859 A | 4/1994 |
| JP | 7031503 A | 2/1995 |
| JP | 7039559 A | 2/1995 |
| JP | 7241307 A | 9/1995 |
| JP | 7255763 A | 10/1995 |
| JP | 7308334 A | 11/1995 |
| JP | 7323039 A | 12/1995 |
| JP | 7324202 A | 12/1995 |
| JP | 8131477 A | 5/1996 |
| JP | 8150162 A | 6/1996 |
| JP | 8154959 A | 6/1996 |
| JP | 8243119 A | 9/1996 |
| JP | 8299016 A | 11/1996 |
| JP | 9010005 A | 1/1997 |
| JP | 9010008 A | 1/1997 |
| JP | 9028409 A | 2/1997 |
| JP | 9051801 A | 2/1997 |
| JP | 9075102 A | 3/1997 |
| JP | 9140405 A | 6/1997 |
| JP | 9191904 A | 7/1997 |
| JP | 9215501 A | 8/1997 |
| JP | 9276308 A | 10/1997 |
| JP | 9313207 A | 12/1997 |
| JP | 10043224 A | 2/1998 |
| JP | 10052472 A | 2/1998 |
| JP | 10155505 A | 6/1998 |
| JP | 10155507 A | 6/1998 |
| JP | 10155509 A | 6/1998 |
| JP | 10155512 A | 6/1998 |
| JP | 10168608 A | 6/1998 |
| JP | 10234759 A | 9/1998 |
| JP | 10328219 A | 12/1998 |
| JP | 11012803 A | 1/1999 |
| JP | 11032805 A | 2/1999 |
| JP | 11056408 A | 3/1999 |
| JP | 11076283 A | 3/1999 |
| JP | 11146802 A | 6/1999 |
| JP | 11169201 A | 6/1999 |
| JP | 11192103 A | 7/1999 |
| JP | 11276203 A | 10/1999 |
| JP | 11276208 A | 10/1999 |
| JP | 11279803 A | 10/1999 |
| JP | 11315401 A | 11/1999 |
| JP | 11318511 A | 11/1999 |
| JP | 2000060934 A | 2/2000 |
| JP | 2000093486 A | 4/2000 |
| JP | 2000116686 A | 4/2000 |
| JP | 2000116696 A | 4/2000 |
| JP | 2000116698 A | 4/2000 |
| JP | 2000232901 A | 8/2000 |
| JP | 2000287705 A | 10/2000 |
| JP | 2000308654 A | 11/2000 |
| JP | 2000316603 A | 11/2000 |
| JP | 2000325376 A | 11/2000 |
| JP | 2000328304 A | 11/2000 |
| JP | 2001000463 A | 1/2001 |
| JP | 2001029374 A | 2/2001 |

(56) References Cited

FOREIGN PATENT DOCUMENTS

| | | |
|---|---|---|
| JP | 2001087297 A | 4/2001 |
| JP | 2001095828 A | 4/2001 |
| JP | 2001104008 A | 4/2001 |
| JP | 2001140102 A | 5/2001 |
| JP | 2001269367 A | 10/2001 |
| JP | 2001299404 A | 10/2001 |
| JP | 2001299792 A | 10/2001 |
| JP | 2001353005 A | 12/2001 |
| JP | 2001355155 A | 12/2001 |
| JP | 2002000302 A | 1/2002 |
| JP | 2002052034 A | 2/2002 |
| JP | 2002065712 A | 3/2002 |
| JP | 2002165611 A | 6/2002 |
| JP | 2002209610 A | 7/2002 |
| JP | 2002209931 A | 7/2002 |
| JP | 2002282011 A | 10/2002 |
| JP | 2002345501 A | 12/2002 |
| JP | 2002355105 A | 12/2002 |
| JP | 2003000629 A | 1/2003 |
| JP | 2003033204 A | 2/2003 |
| JP | 2003052728 A | 2/2003 |
| JP | 2003126130 A | 5/2003 |
| JP | 2003210206 A | 7/2003 |
| JP | 2003250601 A | 9/2003 |
| JP | 2003319804 A | 11/2003 |
| JP | 2004166810 A | 6/2004 |
| JP | 2004167069 A | 6/2004 |
| JP | 2004167144 A | 6/2004 |
| JP | 2004180746 A | 7/2004 |
| JP | 2004201933 A | 7/2004 |
| JP | 2004202074 A | 7/2004 |
| JP | 2004202128 A | 7/2004 |
| JP | 2004215870 A | 8/2004 |
| JP | 2004216087 A | 8/2004 |
| JP | 2004229992 A | 8/2004 |
| JP | 2004242988 A | 9/2004 |
| JP | 2004250796 A | 9/2004 |
| JP | 2004329452 A | 11/2004 |
| JP | 2005000347 A | 1/2005 |
| JP | 2005009011 A | 1/2005 |
| JP | 2005013682 A | 1/2005 |
| JP | 2005021191 A | 1/2005 |
| JP | 2005040571 A | 2/2005 |
| JP | 2005042213 A | 2/2005 |
| JP | 2005052593 A | 3/2005 |
| JP | 2005152218 A | 6/2005 |
| JP | 2005160560 A | 6/2005 |
| JP | 2005245471 A | 9/2005 |
| JP | 2005245571 A | 9/2005 |
| JP | 2005279188 A | 10/2005 |
| JP | 2005281917 A | 10/2005 |
| JP | 2005287726 A | 10/2005 |
| JP | 2005305063 A | 11/2005 |
| JP | 2005305085 A | 11/2005 |
| JP | 2005349225 A | 12/2005 |
| JP | 2006000403 A | 1/2006 |
| JP | 2006000549 A | 1/2006 |
| JP | 2006043369 A | 2/2006 |
| JP | 2006043376 A | 2/2006 |
| JP | 2006055591 A | 3/2006 |
| JP | 2006081797 A | 3/2006 |
| JP | 2006130248 A | 5/2006 |
| JP | 2006132037 A | 5/2006 |
| JP | 2006141651 A | 6/2006 |
| JP | 2006187545 A | 7/2006 |
| JP | 2006247335 A | 9/2006 |
| JP | 2006249623 A | 9/2006 |
| JP | 2006263407 A | 10/2006 |
| JP | 2006271915 A | 10/2006 |
| JP | 2006288491 A | 10/2006 |
| JP | 2006289003 A | 10/2006 |
| JP | 2006314656 A | 11/2006 |
| JP | 2006326264 A | 12/2006 |
| JP | 2007090017 A | 4/2007 |
| JP | 2007097846 A | 4/2007 |
| JP | 2007130369 A | 5/2007 |
| JP | 2007167180 A | 7/2007 |
| JP | 2007215967 A | 8/2007 |
| JP | 2007229378 A | 9/2007 |
| JP | 2007236905 A | 9/2007 |
| JP | 2007244786 A | 9/2007 |
| JP | 2007252585 A | 10/2007 |
| JP | 2007313043 A | 12/2007 |
| JP | 2007319201 A | 12/2007 |
| JP | 2007330743 A | 12/2007 |
| JP | 2008000244 A | 1/2008 |
| JP | 2008023258 A | 2/2008 |
| JP | 2008023300 A | 2/2008 |
| JP | 2008061960 A | 3/2008 |
| JP | 2008093399 A | 4/2008 |
| JP | 2008121177 A | 5/2008 |
| WO | WO8504558 A1 | 10/1985 |
| WO | WO8901745 A1 | 3/1989 |
| WO | WO9211777 A1 | 7/1992 |
| WO | WO9401496 A1 | 1/1994 |
| WO | WO9629988 A1 | 10/1996 |
| WO | WO9641523 A1 | 12/1996 |
| WO | WO9721404 A1 | 6/1997 |
| WO | WO9858631 A1 | 12/1998 |
| WO | WO9943227 A1 | 9/1999 |
| WO | WO0006036 A1 | 2/2000 |
| WO | WO0015163 A1 | 3/2000 |
| WO | WO 00/18313 | 4/2000 |
| WO | WO0121119 A1 | 3/2001 |
| WO | WO0191674 A1 | 12/2001 |
| WO | WO0211573 A1 | 2/2002 |
| WO | WO0217840 A1 | 3/2002 |
| WO | WO0241944 A2 | 5/2002 |
| WO | WO02098254 A1 | 12/2002 |
| WO | WO03045179 A2 | 6/2003 |
| WO | WO03099144 A1 | 12/2003 |
| WO | WO03099344 A2 | 12/2003 |
| WO | WO2004056305 A2 | 7/2004 |
| WO | WO2004058286 A1 | 7/2004 |
| WO | WO2004069866 A1 | 8/2004 |
| WO | WO2004078220 A2 | 9/2004 |
| WO | WO2004107895 A1 | 12/2004 |
| WO | WO2005013745 A1 | 2/2005 |
| WO | WO2005034670 A2 | 4/2005 |
| WO | WO2005039439 A2 | 5/2005 |
| WO | WO2005056050 A1 | 6/2005 |
| WO | WO2005079828 A2 | 9/2005 |
| WO | WO2005102092 A1 | 11/2005 |
| WO | WO2006030546 A1 | 3/2006 |
| WO | WO2006047227 A1 | 5/2006 |
| WO | WO2006058140 A2 | 6/2006 |
| WO | WO2006066419 A1 | 6/2006 |
| WO | WO2006069451 A1 | 7/2006 |
| WO | WO2006069452 A1 | 7/2006 |
| WO | WO2006088412 A1 | 8/2006 |
| WO | WO2006107779 A2 | 10/2006 |
| WO | WO2006120385 A2 | 11/2006 |
| WO | WO2007008348 A2 | 1/2007 |
| WO | WO2007021865 A2 | 2/2007 |
| WO | WO2007025520 A1 | 3/2007 |
| WO | WO2007089617 A2 | 8/2007 |
| WO | WO2007098057 A2 | 8/2007 |
| WO | WO2007106498 A2 | 9/2007 |
| WO | WO2008006929 A1 | 1/2008 |
| WO | WO2008102405 A1 | 8/2008 |
| WO | WO2008118426 A1 | 10/2008 |
| WO | WO2009/018527 | 2/2009 |
| WO | WO 2010/093696 | 8/2010 |
| WO | 2010106507 | 9/2010 |

OTHER PUBLICATIONS

H. Kelikian, M.D., "Miscellaneous Methods", Hallux Valgus, Allied Deformities of the Forefoot and Metatarsalgia, 1965, pp. 253-261, W.B. Saunders Company, Philadelphia and London.

Coughlin et al., "Proximal metatarsal osteotomy and distal soft tissue reconstruction as treatment for hallux valgus deformity", Keio J. Med. 54(2) p. 60-65.

(56) References Cited

OTHER PUBLICATIONS

RetroButton™ ACL Reconstruction, Arthrex® 8 pages, ©Copyright Arthrex Inc., 2007.
Mini TightRope® Surgical Technique, © Copyright 2007, 6 pages.
International Search Report and Written Opinion issued in PCT/US2010/049583, mailed Dec. 10, 2010, 13 pages.
International Search Report and Written Opinion issued in PCT/US2010/023757, mailed Jun. 2, 2010, 16 pages.
International Search Report and Written Opinion issued in PCT/US2011/021924, mailed Mar. 16, 2011, 11 pages.
Invitation to Pay Additional Fees issued in PCT/US2011/039041, mailed Sep. 6, 2011, 4 pages.
International Search Report and Written Opinion issued in PCT/US2011/039041, mailed Oct. 19, 2011, 14 pages.

* cited by examiner

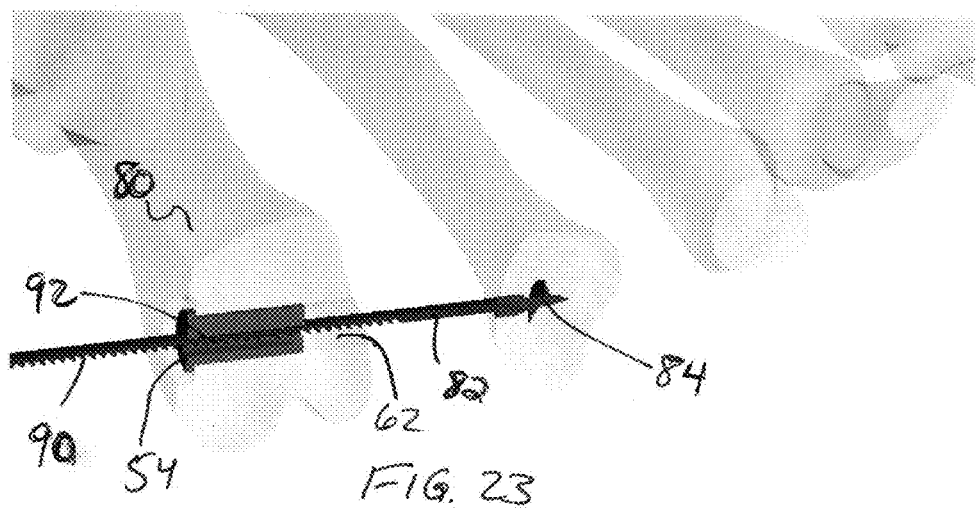
FIG. 23
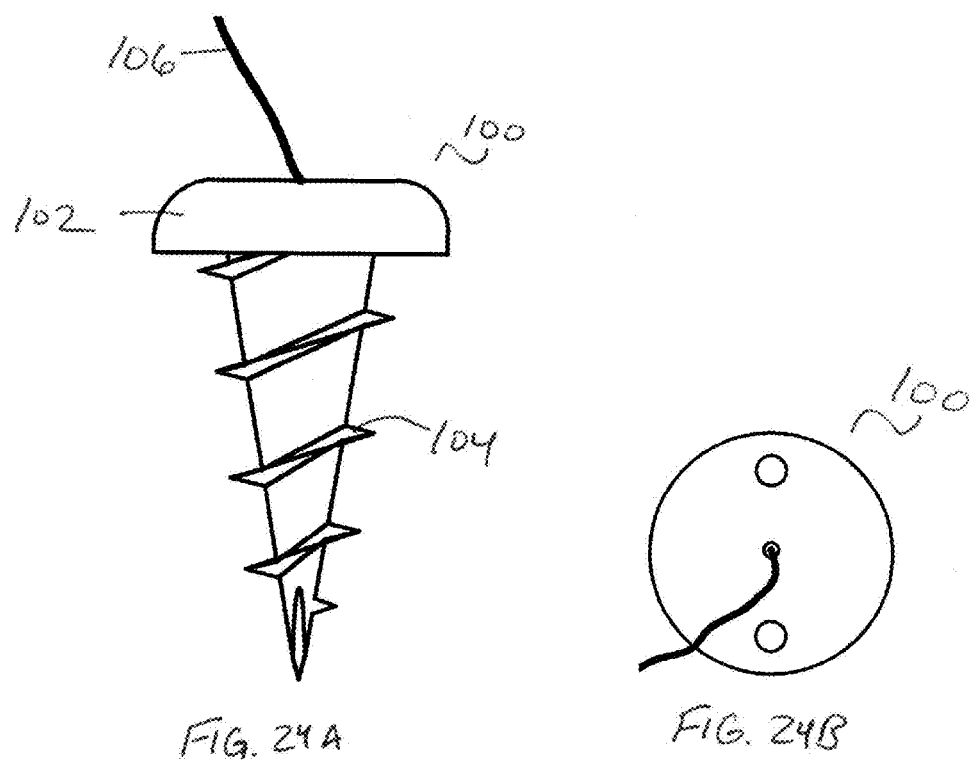
FIG. 24A
FIG. 24B

METHODS AND DEVICES FOR TREATING HALLUX VALGUS

FIELD OF THE INVENTION

The various embodiments disclosed herein relate to methods and devices for treating a structural bone and joint deformity. More specifically, certain embodiments relate to systems and methods for correcting such deformity, including hallux valgus.

BACKGROUND OF THE INVENTION

Hallux valgus deformities in the human foot typically relate to at least one of two conditions: a deviated position of the great toe where the great toe leans in towards the second toe (also referred to as the "hallux valgus angle" or "HV angle" as described below), and a deviation in the angle between the first and second metatarsal bones of the foot (also referred to as the "intermetatarsal angle" or "IM angle"). The most commonly used medical terms associated with these deformities are "hallux valgus" and "hallux abducto valgus," where "hallux" refers to the great toe, "valgus" refers to the deformity in the frontal plane of an abnormal rotation of the great toe, and "abducto" refers to the abnormal slant or leaning of the great toe towards the second toe, as shown in FIGS. 1A and 1B. Hallux valgus is also commonly referred to in laymen's terminology as a "bunion," but the term "bunion" is more properly understood as the pathological bump, callous, and/or inflammation on the side of the great toe joint associated with either a bursal sac or structural deformity of the great toe as described above.

Various treatments for hallux valgus and/or bunions exist. Various surgical procedures may address some combination of removing the abnormal bony enlargement of the first metatarsal bone, realigning portions of the first metatarsal bone relative to the adjacent metatarsal bone via an osteotomy, straightening the first metatarsal bone relative to the adjacent toes through manipulations of the joint capsule, realigning the cartilaginous surfaces of the great toe joint, and/or repositioning the sesamoid bones beneath the first metatarsal bone. Other treatments can include bunion pads and external splints. All of these known treatments have shortcomings in either effectiveness (pads and splints) or invasiveness (the surgical procedures). With respect to the existing surgical procedures, the vast majority require an osteotomy for realignment of portions of the first metatarsal bone, which leads to long recovery and the need for patients to wear a cast or surgical boot for weeks following the operation, as well as the need to "stage" the procedure if both feet require surgical correction, i.e., treating one foot in a first surgery and then the other in a subsequent second surgery. Further, the surgical patients are left with a significant scar and poor cosmesis. In addition, studies have highlighted that as many as 30% of bunion surgery patients are unhappy with the result and nearly 10% have post-surgical complications. Finally, the surgical procedures are costly, requiring anesthesia, a lengthy operating time, and multiple trained medical staff.

BRIEF SUMMARY OF THE INVENTION

Discussed herein are various treatment devices for treating structural bone deformities.

In Example 1, a method of treating hallux valgus comprises positioning a first capsule anchor in a medial side of a second metatarsophalangeal ("MTP") joint capsule, positioning a second capsule anchor in a lateral side of a first MTP joint capsule, and urging the second capsule anchor toward the first capsule anchor. The first capsule anchor is coupled to a first end of a first tether and the second capsule anchor is coupled to a second end of the first tether.

Example 2 relates to the method of treating hallux valgus according to Example 1, wherein urging the second capsule anchor toward the first capsule anchor comprises shortening the length of the tether.

Example 3 relates to the method of treating hallux valgus according to Example 2, wherein shortening the length of the tether comprises using a slip knot to shorten the length of the tether.

Example 4 relates to the method of treating hallux valgus according to Example 1, wherein urging the second capsule anchor toward the first capsule anchor further comprises creating a tension in the first tether.

Example 5 relates to the method of treating hallux valgus according to Example 1, and further comprises positioning a third capsule anchor in a proximal portion on a medial side of a first MTP joint capsule, positioning a fourth capsule anchor in a distal portion on the medial side of the first MTP joint capsule, and urging the fourth capsule anchor toward the third capsule anchor. The third capsule anchor is coupled to a first end of a second tether and the fourth capsule anchor is coupled to a second end of the second tether.

Example 6 relates to the method of treating hallux valgus according to Example 5, wherein positioning the first, second, third, and fourth capsule anchors comprises inserting the first, second, third, and fourth capsule anchors with an application device. The application device comprises an elongate body having a lumen disposed therethrough, and each of the first, second, third, and fourth capsule anchors are initially disposed within the lumen.

Example 7 relates to the method of treating hallux valgus according to Example 1, wherein positioning the first capsule anchor comprises inserting a sharp distal tip of an application device into the medial side of the second MTP joint capsule and urging an advancement rod disposed within the lumen of the application device from a proximal position to a distal position, thereby urging the first capsule anchor out of the lumen through an opening defined in the sharp distal tip and into an appropriate position in relation to the second MTP joint capsule. The application device comprises an elongate body comprising a lumen disposed therethrough.

Example 8 relates to the method of treating hallux valgus according to Example 7, wherein positioning the second capsule anchor comprises inserting the sharp distal tip of the application device into the lateral side of the first MTP joint capsule, and urging the advancement rod from the proximal position to the distal position, thereby urging the second capsule anchor out of the lumen through the opening defined in the sharp distal tip and into an appropriate position in relation to the first MTP joint capsule.

In Example 9, a method of treating hallux valgus comprises forming a hole through a first metatarsal bone, attaching a first anchor to the second metatarsal, positioning a second anchor comprising a bone anchor in the first opening on the medial side of the first metatarsal bone, and urging the bone anchor toward the first anchor. The hole has a first opening on a medial side of the bone and a second opening on a lateral side of the bone. The first anchor is coupled to a first end of a tether, the bone anchor is coupled to a second end of the tether, and the tether is disposed through the hole.

Example 10 relates to the method of treating hallux valgus according to Example 9, wherein the first anchor comprises a capsule anchor, and attaching the first anchor to the second metatarsal comprises positioning the first anchor in the medial side of the second MTP joint capsule.

Example 11 relates to the method of treating hallux valgus according to Example 10, wherein positioning the first anchor in the medial side of the second MTP joint capsule further comprises inserting an application device through the hole in the first metatarsal bone, inserting the sharp distal tip of the application device into the medial side of the second MTP joint capsule, and urging an advancement rod disposed within the lumen of the application device from a proximal position to a distal position, thereby urging the first anchor out of the lumen through an opening defined in the sharp distal tip and into an appropriate position in relation to the second MTP joint capsule. The application device comprising an elongate body comprising a sharp distal tip and a lumen disposed through the elongate body.

Example 12 relates to the method of treating hallux valgus according to Example 11, further comprising withdrawing the application device back through the hole in the first metatarsal bone after positioning the first anchor.

Example 13 relates to the method of treating hallux valgus according to Example 9, wherein positioning the bone anchor in the first opening on the medial side of the first metatarsal bone further comprises screwing a threaded portion of the bone anchor into the first opening.

Example 14 relates to the method of treating hallux valgus according to Example 9, further comprising forming an incision in the medial side of the first MTP capsule and laying back cut portions of the first MTP capsule prior to forming the hole in the first metatarsal bone.

Example 15 relates to the method of treating hallux valgus according to Example 14, further comprising removing at least a portion of an eminence on the medial side of the first metatarsal bone after forming the incision and prior to forming the hole.

Example 16 relates to the method of treating hallux valgus according to Example 9, wherein urging the bone anchor toward the first anchor further comprises creating a tension in the first tether.

Example 17 relates to the method of treating hallux valgus according to Example 9, wherein the first anchor comprises a bone anchor, wherein attaching the first anchor to the second metatarsal comprises screwing a threaded portion of the first anchor into bone of the second metatarsal.

In Example 18, a method of reducing an HV angle comprises forming an incision in the medial side of the first MTP capsule, laying back cut portions of the first MTP capsule, positioning a bone anchor in the medial side of the first metatarsal bone, threading a first end of at least one suture through an aperture in the bone anchor, threading a second end of the at least one suture through at least one cut portion of the first MTP capsule, threading the second end of the at least one suture through the aperture in the bone anchor, and tightening the at least one suture by pulling at least one of the first and second ends of the suture, whereby the at least one cut portion is urged toward the bone anchor.

Example 19 relates to the method of reducing an HV angle according to Example 18, further comprising removing at least a portion of an eminence on the medial side of the first metatarsal bone after forming the incision.

Example 20 relates to the method of reducing an HV angle according to Example 18, further comprising forming a hole in the medial side of the first metatarsal bone, wherein the positioning the bone anchor further comprises positioning the bone anchor in the hole.

Example 21 relates to the method of reducing an HV angle according to Example 20, wherein positioning the bone anchor further comprises screwing threads of the bone anchor into the hole.

Example 22 relates to the method of reducing an HV angle according to Example 18, wherein the tightening the at least one suture further comprises pulling the first MTP capsule over the bone anchor.

Example 23 relates to the method of reducing an HV angle according to Example 22, further comprising suturing the incision on the first MTP capsule.

Example 24 relates to the method of reducing an HV angle according to Example 22, wherein the tightening the at least one suture results in the first MTP capsule being pulled tight, wherein the first MTP capsule being pulled tight applies a tension to the medial side of the MTP joint, thereby reducing the HV angle.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE DRAWINGS

FIG. 23 is a cross-sectional depiction of another implantable bone deformity treatment device, according to one embodiment.

FIG. 24A is a front view of a bone anchor, according to one embodiment.

FIG. 24B is a top view of the bone anchor of FIG. 24A, according to one embodiment.

DETAILED DESCRIPTION

Various embodiments disclosed herein relate to methods and devices for treating a bone deformity, such as, for example, hallux valgus (bunions). More specifically, various embodiments herein relate to bone deformity treatments using tension or connection systems and methods for anchoring or otherwise coupling metatarsophalangeal ("MTP") joint capsules such as the first and second MTP joint capsules. Some of the various device and method embodiments disclosed herein operate at least in part by anchoring or coupling to the MTP joint capsules, thereby minimizing the invasiveness of the bone deformity treatment. Other device and method embodiments operate by anchoring or coupling to the metatarsal bones. Further alternatives may have one component that anchors or couples to an MTP joint capsule while another component anchors or couples to a metatarsal bone. As such, various embodiments disclosed herein provide systems and methods for implantation of treatment devices (also referred to herein as "ties" or "anchoring components") and treatment of hallux valgus with reduced trauma and quicker recovery in comparison to known systems and treatments.

Figure 1:
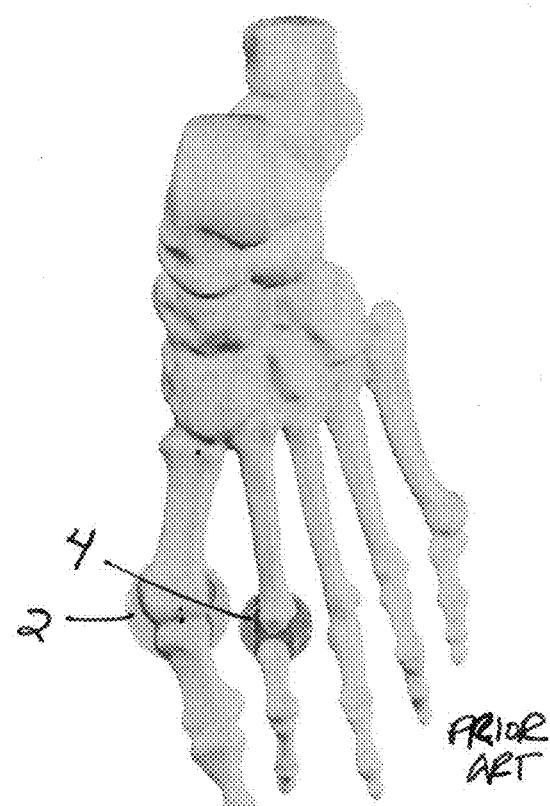
FIG. 1 is a schematic depiction of a foot exhibiting hallux valgus.

As shown in FIG. 1, it is understood that there is a capsule (which shall be referred to herein as "MTP capsules") surrounding each of the metatarsophalangeal ("MTP") joints in the foot. Each MTP capsule operates to maintain the adjacent bone joint surfaces in proximity to each other and is made of ligamentous tissue, which is typically very durable and resilient. In this schematic, the capsule 2 surrounding the first MTP joint and the capsule 4 surrounding the second MTP joint are shown. Various embodiments disclosed herein relate to methods and systems for attaching anchors or attachment components to these capsules. The term "anchor" and "attachment component" is intended for purposes of this application to mean any component or device that can be used with any of the treatment device embodiments disclosed herein for anchoring or coupling such treatment devices to various parts of a foot, with "capsule anchor" intended to mean any component or device that can be used for anchoring or coupling a treatment device to an MTP capsule, and "bone anchor" intended to mean any component or device that can be used for anchoring or coupling a treatment device to a bone. It is understood that the MTP capsules 2, 4 as depicted in FIG. 1 and the MTP capsules depicted in the other figures discussed herein are depicted in an exaggerated form for easy depiction and explanation of the methods and devices disclosed herein. That is, the MTP capsules as depicted are proportionally larger and more prominent that actual MTP capsules.

Figure 2:
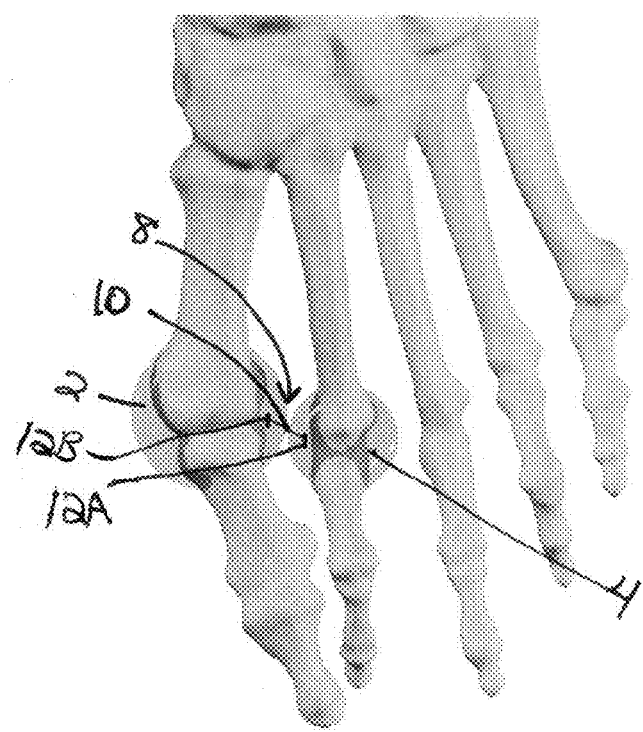
FIG. 2 is a schematic depiction of an implantable bone deformity treatment device in a foot exhibiting hallux valgus, according to one embodiment.

According to one embodiment as shown in FIG. 2, the first and second MTP joint capsules 2,4 can be anchored to each other using a first treatment device 8 comprising a first capsule anchor 12A and a second capsule anchor 12B. The first capsule anchor 12A is attached or otherwise anchored in the second MTP joint capsule 4, while the second capsule anchor 12B is anchored in the first MTP joint capsule 2, and the two anchors 12A, 12B are attached by a tether 10 that urges the first MTP joint capsule towards the second MTP joint capsule.

It is understood that "tether," as used herein, is intended to mean any elongate component for use with medical devices such as suture or thread or any other such material or device that can be tensioned between two components such as anchors to treat bone deformations. The tether could be fabricated from a variety of suitable implantable materials. Such materials include monofilament or multi-filament structures such as yarns, braids, or weaves. In accordance with one embodiment, the tether has lateral flexibility, and as such, materials that could provide lateral flexibility include polyester (such as Dacron™), ultra-high molecular weight polyethylene (UHMWPE), high strength expanded PTFE, or polycarbonate urethane. Other materials include those exhibiting higher elasticity, such as silicone rubber, PEBA such as Pebax™, Kraton™ polymers, polyurethane, latex, or any other elastomeric materials. In other implementations, the tether embodiments can be made of a bio-absorbable material such as poly-lactic acid, poly-L-lactic acid, or any known bioabsorbable material such as those used in biodegradable sutures. It is understood that various combinations of the above materials are also contemplated.

Figure 3:
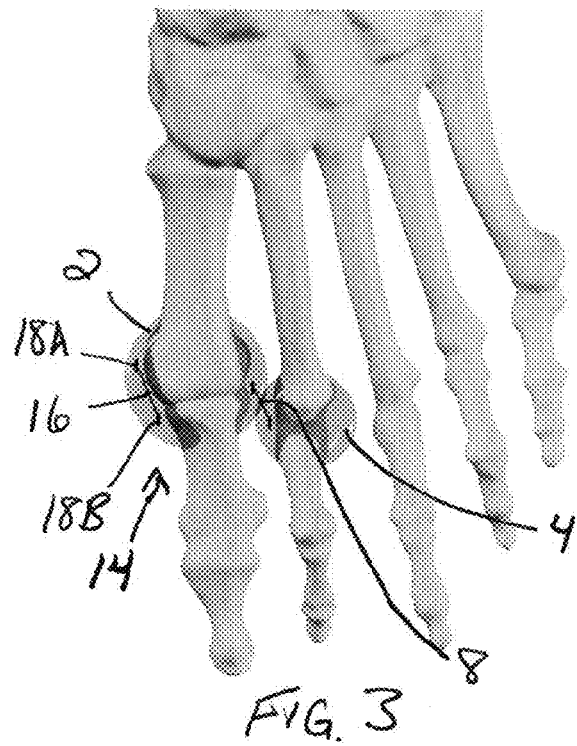
FIG. 3 is a schematic depiction of two implantable bone deformity treatment devices in a foot exhibiting hallux valgus, according to one embodiment.

FIG. 3 depicts another embodiment in which a second treatment device 14 is used in conjunction with the first treatment device 8. The first device 8 is attached as described with respect to FIG. 2. In addition, treatment device 14 is placed in the first MTP joint capsule on the medial side of the capsule as shown. More specifically both capsule anchors 18A and 18B are anchored in the medial side of the capsule 2 and coupled to each other with a tether 16.

Figure 4:
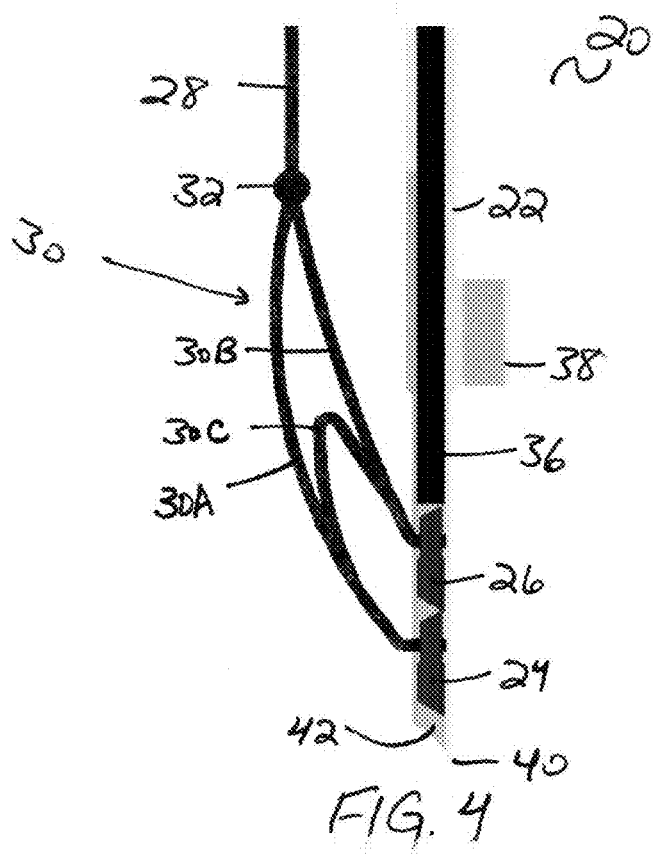
FIG. 4 is a cross-sectional depiction of an application device, according to one embodiment.

Various device and method embodiments as disclosed herein can be used to anchor these types of anchoring components into the MTP joint capsules. In one embodiment as shown in FIG. 4, an application device 20 can be used to implant the anchoring components. The application device in this embodiment has a cannula 22 with a sharpened distal tip 40. The cannula 22 is configured to receive at least one capsule anchor within the lumen of the cannula 22. For example, in the device depicted in FIG. 4, there are two capsule anchors 24, 26 disposed within the lumen 42 of the device 20. Each of the anchors 24, 26 is coupled to a tether 28. In this embodiment, the tether 28 has a loop 30 at its distal end that is coupled to the tether 28 at the slip knot 32. The loop 30 is threaded through capsule anchors 24 and 26 such that there are three segments of the loop 30: a first segment 30A between the slip knot 32 and the first capsule anchor 24, a second segment 30B between the slip knot 32 and the second capsule anchor 26, and a third segment 30C between the first and second anchors 24, 26. The loop 30 is threaded through appropriate holes or lumens or any other appropriate component to receive a tether in the capsule anchors 24, 26 such that the loop 30 can be moveable in relation to each of the anchors 24, 26.

In one embodiment, the application device 20 has a slot (not visible) running along a side of the device 20 at the distal end. This slot is in communication with the lumen 42 such that both of the loop segments 30A, 30B, 30C can extend out of the lumen 42 through the slot as shown in FIG. 4 As will be explained in further detail below, once the capsule anchors 24, 26 are both implanted as desired, the loop 30 and the slip knot 32 make it possible to pull on the tether 28 to tighten the loop 30 and thereby apply tension urging the two implanted anchors 24, 26 together.

Continuing with FIG. 4, the application device 20 also has an advancer rod 36 that is configured to be moveably received within the lumen 42 such that the rod 36 can be advanced toward the distal end of the device 20, thereby urging one or more capsule anchors out of the distal tip. According to one alternative embodiment, the device 20 can also have a handle (not shown) at the proximal end of the device 20 that facilitates movement of the advancer rod 36 in relation to the device 20. Further, the application device 20 has an external projection 38 that is positioned at an appropriate point along the cannula 22 to serve as a stop mechanism when the distal tip 40 has been inserted into the appropriate position within the capsule.

Figure 5:
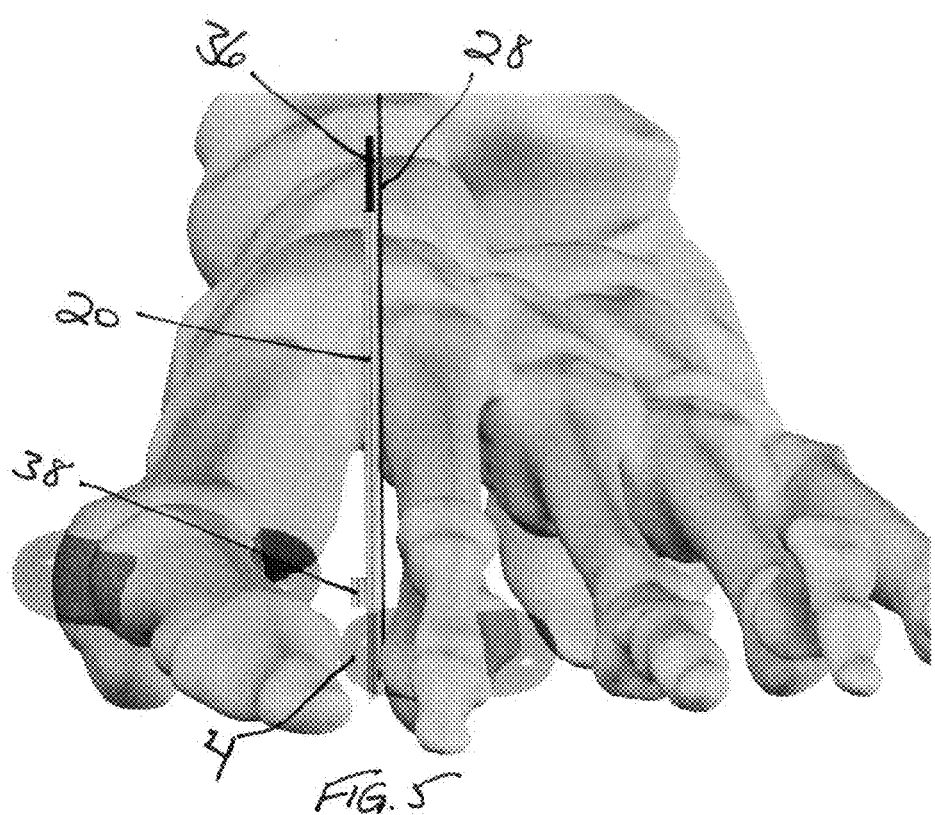
FIG. 5 is a perspective view of an application device during implantation of an implantable bone deformity treatment device, according to one embodiment.

As discussed above, the application device 20 can be used to implant a treatment device into one or more MTP joint capsules. FIG. 5, according to one exemplary implementation, depicts a first step of the use of the application device 20 to implant an anchored tie such as either of the ties depicted in FIG. 3. In this embodiment, the application device 20 is positioned above the second MTP joint capsule 4 and inserted into the capsule 4 from a position above the capsule 4. The distal tip is inserted into the medial side of that capsule 4, as shown. The tip is inserted until the projection 38 is urged against the top portion of the capsule 4, thereby providing resistance to the user or surgeon and indicating that the device 20 is appropriately positioned. During this insertion step, the main tether 28 extends along the outer surface of the device 20 and a distal portion of that tether 28 is positioned through the slot (not shown) at the distal tip of device 20 and coupled to at least one capsule anchor positioned inside the lumen of the device 20 (as best shown in FIG. 4). While skin and other connective tissues are not shown in the figures, it is understood that the implantation procedures disclosed herein can be performed by forming a small incision in the skin at the appropriate location.

Figure 6:
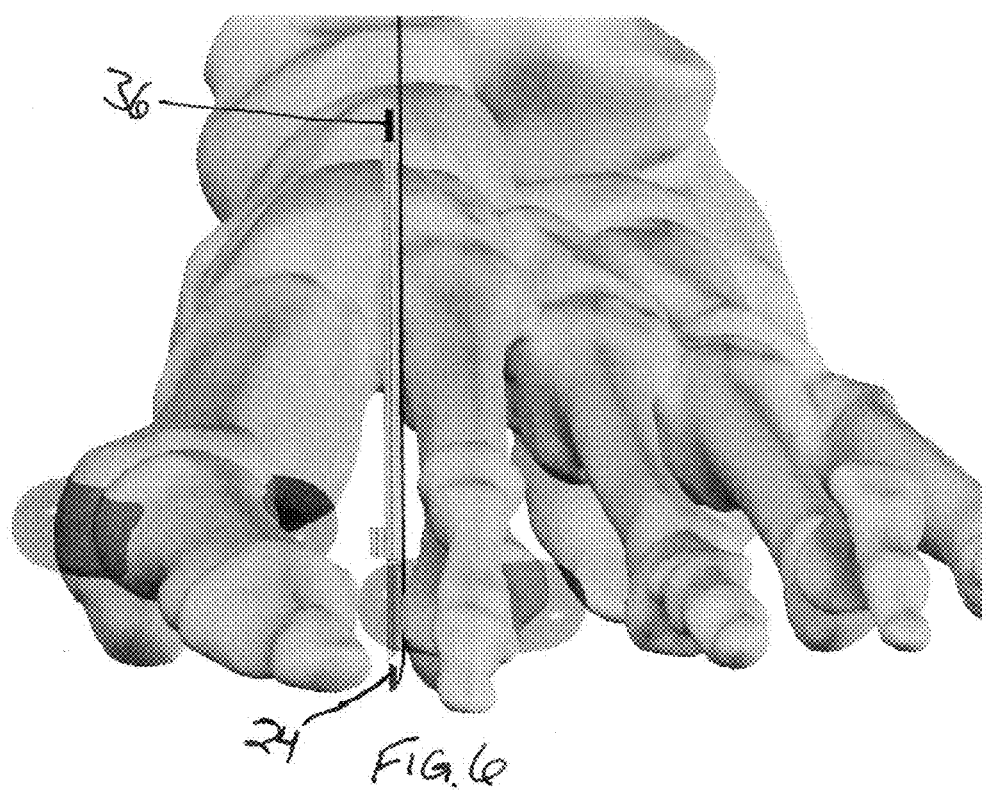
FIG. 6 is a perspective view of the application device of FIG. 5 during implantation of the implantable bone deformity treatment device, according to one embodiment.

In accordance with one implementation as shown in FIG. 6, after the device 20 has been appropriately positioned, the capsule anchor 24 can be deployed. This deployment occurs by urging the advancer rod 36 in a distal direction, thereby urging the distal-most capsule anchor 24 (as best shown in FIG. 4) out of the distal tip of the application device 20. Once the anchor 24 has been deployed, the user can pull proximally on the main tether 28, thereby urging the tether and the capsule anchor 24 in a proximal direction until the anchor is urged against a bottom portion of the capsule (or up to a particular location within the capsule itself). Once the user feels the resistance along the main tether 28 as a result of the capsule anchor being positioned appropriately against the capsule, the user can remove the application device 20 by urging the device 20 proximally to remove the distal tip from the capsule. As the application device 20 is removed in such fashion, the capsule anchor 24 and the tether loop 30 (as best shown in FIG. 7) coupled to the anchor 24 remain in position within or attached to the medial capsule.

Figure 7:
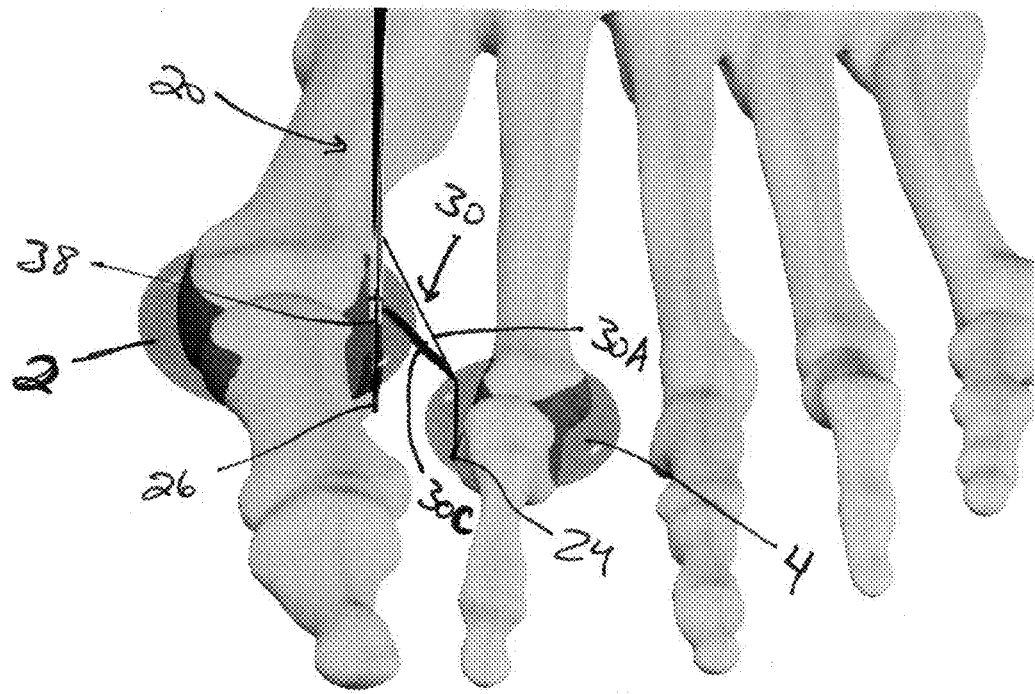
FIG. 7 is a perspective view of the application device of FIG. 5 during implantation of the implantable bone deformity treatment device, according to one embodiment.

The next step, according to one embodiment as shown in FIG. 7, is the implantation of the second capsule anchor 26 in the MTP capsule 2 of the first metatarsal. As with the implantation of the first capsule anchor 24, the second capsule anchor 26 is positioned by first inserting the application device 20 into the MTP capsule 2, but in this case, the insertion point is the lateral side of the first MTP capsule 2. The application device 20 is inserted until the user again feels the resistance that occurs when the projection 38 contacts the MTP capsule 2. As shown in FIG. 7, the loop 30 remains loosely threaded through anchors 24, 26 such that the first segment 30A extends to the anchor 24 and the third segment 30C extends between the anchor 24 and MTP capsule 4 on one side and the anchor 26 and MTP capsule 2 on the other. At this point, the user can actuate the advancer rod 36 by urging it the distal direction, thereby urging the anchor 26 out of the distal end of the application device 20. Once the anchor 26 has been deployed, the user can withdraw the application device 20 in a similar fashion as described above by moving it in a proximal direction, thereby leaving the anchor 26 in place. Either before or after the application device 20 has been removed, the user again pulls the main tether 28 in a proximal direction, thereby securing the anchor 26 against or within the first MTP capsule 2.

Figure 8:
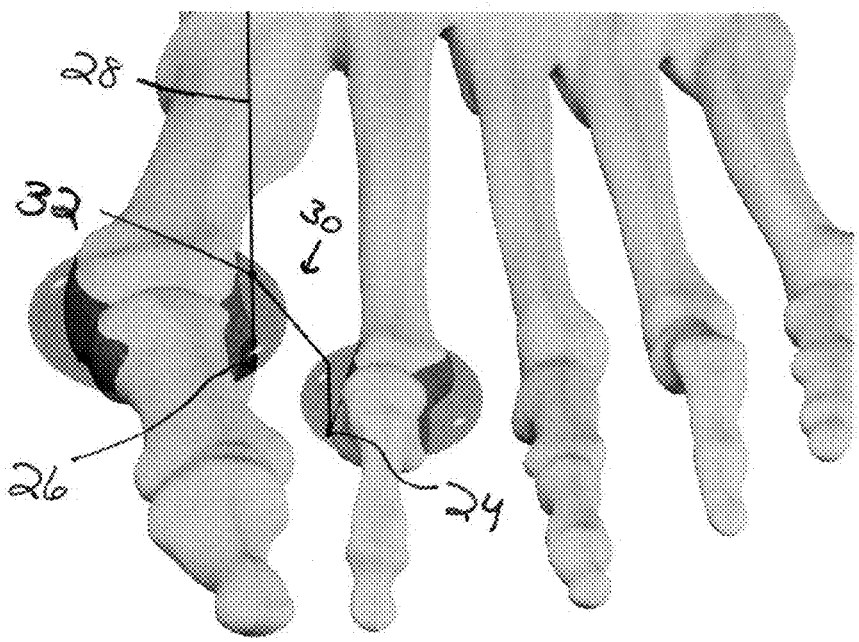
FIG. 8 is a perspective view of the application device of FIG. 5 during implantation of the implantable bone deformity treatment device, according to one embodiment.

According to one embodiment, FIG. 8 depicts the two capsule anchors 24, 26 and the main tether 28 after both anchors 24, 26 have been implanted and the application device 20 has been removed. Note that the loop 30 is still moveably coupled to the anchors 24, 26. The final step, according to one embodiment, is to form a tight tether connection between the two capsule anchors 24, 26 by pulling the tether 28 in the proximal direction in relation to the anchors 24, 26 and the slipknot 32, thereby tightening the loop 30 such that a tension is created urging the second anchor 26 toward the first anchor (and thereby urging the first MTP capsule 2 toward the second MTP capsule 4). When the tension between the two anchors 24, 26 has reached the desired amount, the main tether 28 can be cut at the slipknot 32 and the slipknot 32 can be fixed in place by any known method.

The end result of this procedure is two implanted capsule anchors 24, 26 coupled to each other by a tensioned tether similar to the anchoring component 8 depicted in FIG. 2. The anchoring component 8 as shown in FIG. 2 applies a force urging the two capsule anchors 24, 26 together, thereby urging the two MTP capsules 2, 4 together. Thus, the anchoring component 8 causes the two metatarsal bones to be brought together into closer proximity, reducing the IM angle. For many patients, this treatment (the implantation of the treatment device 8) suffices to correct the underlying deformity. Alternatively, in other patients, additional corrective measures may need to be taken, such as straightening the HV angle (toe angle). This correction may be accomplished by conventional means, such as capsulorraphy, whereby structures that overly tighten the lateral side of the capsule of the first MTP joint are cut, and/or the medial aspect of the capsule is surgically "tightened". Other adjunctive corrective measures are contemplated as well. It is understood that any of these known methods can be used in conjunction with any of the methods and devices disclosed herein.

It is understood that the capsule anchors 24, 26 described above and the additional capsule anchor embodiments described and depicted elsewhere herein are deployable anchors that move between an undeployed position and a deployed position within the capsule, resulting in attachment of the anchor within or to the capsule. More specifically, the capsule anchors 24, 26 are elongate anchors. In one implementation, the elongate capsule anchors 24, 26 are deployed by rotation of the anchors 24, 26. Alternatively, any capsule anchor embodiment described herein can be an expandable component or device that is expanded upon implantation by any suitable expansion means, thereby fixing or attaching the anchor within or against the capsule. In a further alternative, any capsule anchor contemplated herein can be any device or component configured to be able to attach to, against, or adjacent to an MTP capsule.

It is understood that the capsule anchors contemplated herein can be made of any known material for implantable medical components or devices. In one embodiment, the anchors can be made of a relatively rigid material such as stainless steel, titanium, a rigid polymer such as PEEK, or the like.

As described above in connection with FIG. 3, one such adjunctive measure in accordance with one embodiment is—in combination with the first anchoring component 8—the implantation of a second anchoring component 14 within the medial capsule 2 of the first MTP joint as shown. Such an anchoring component 14 would serve to "tighten" or foreshorten the medial portion of the capsule 2, which will bring the first toe into straighter alignment with the first metatarsal bone, as shown. The combination of the first anchoring component 8 between the two MTP capsules 2, 4 and the second anchoring component 14 in the medial portion of the first MTP capsule 2 serves to treat, and in many cases correct, both underlying aspects of HV, namely the IM angle and the HV angle. In certain embodiments, the implantation of both the first and second anchoring components 8, 14 could be particularly suitable in patients who do not yet possess a large eminence, but rather suffer primarily from high HV angle and/or high IM angle.

In another embodiment, the joint deformation can be treated or corrected using a capsule anchor attached to the second MTP capsule that is tethered to a bone anchor implanted into the first metatarsal bone. In one exemplary embodiment shown in FIG. 9, the capsule anchor 50 is implanted in the second MTP capsule 4 and the bone anchor 54 is positioned within a hole (not shown) drilled in the first metatarsal, and a tensioned tether 52 is attached to both the capsule anchor 50 and the bone anchor 54.

Figure 9:
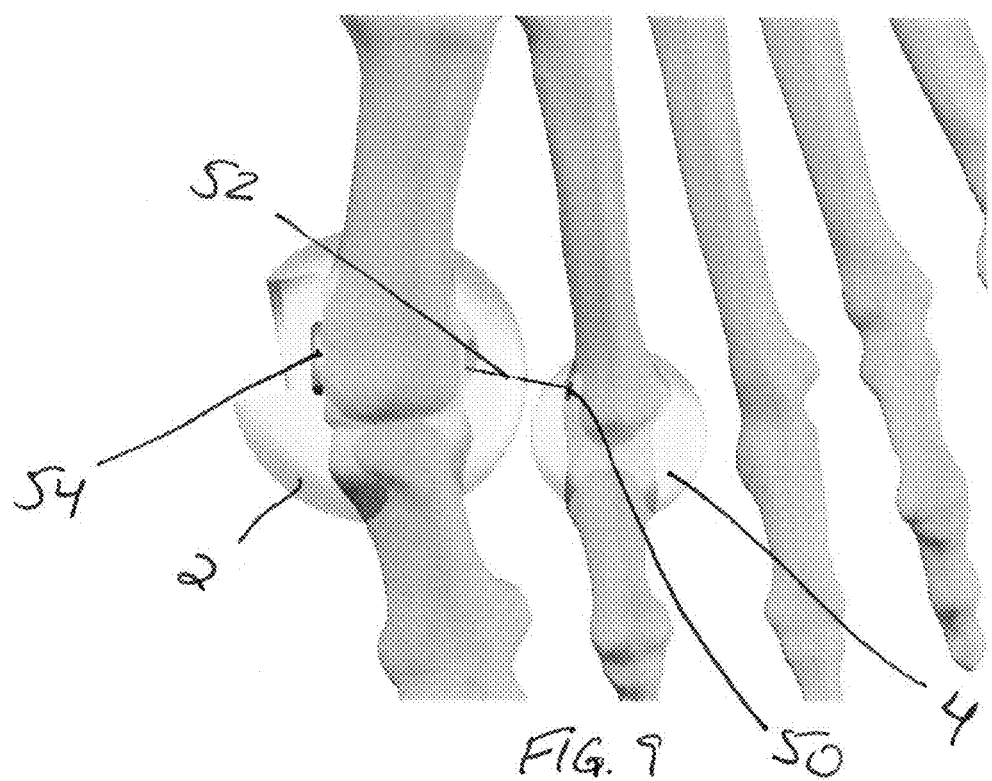
FIG. 9 is a schematic depiction of another implementation of an implantable bone deformity treatment device in a foot exhibiting hallux valgus, according to one embodiment.
Figure 10:
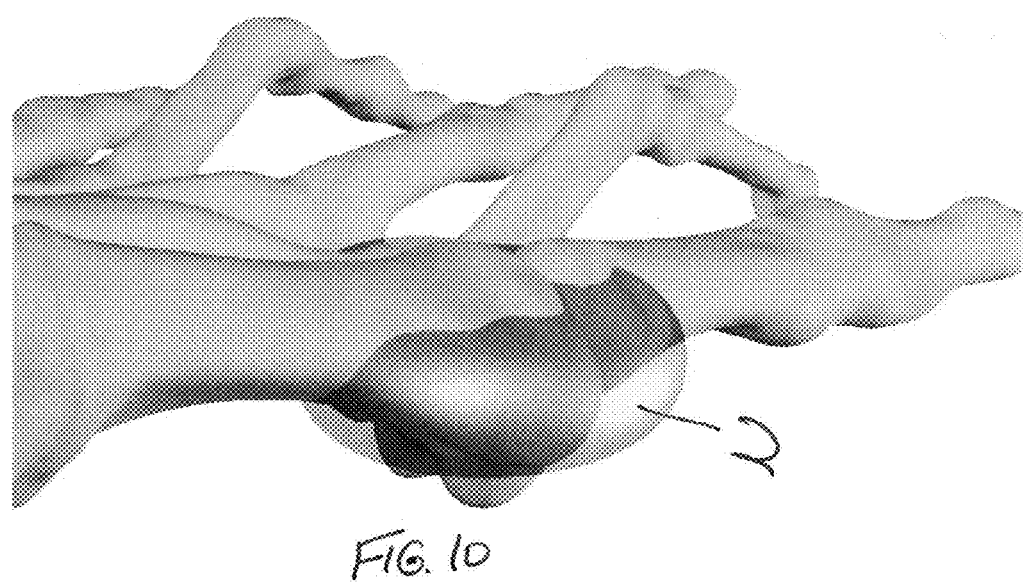
FIG. 10 is a schematic depiction of a foot and specifically of a first MTP capsule.
Figure 11:
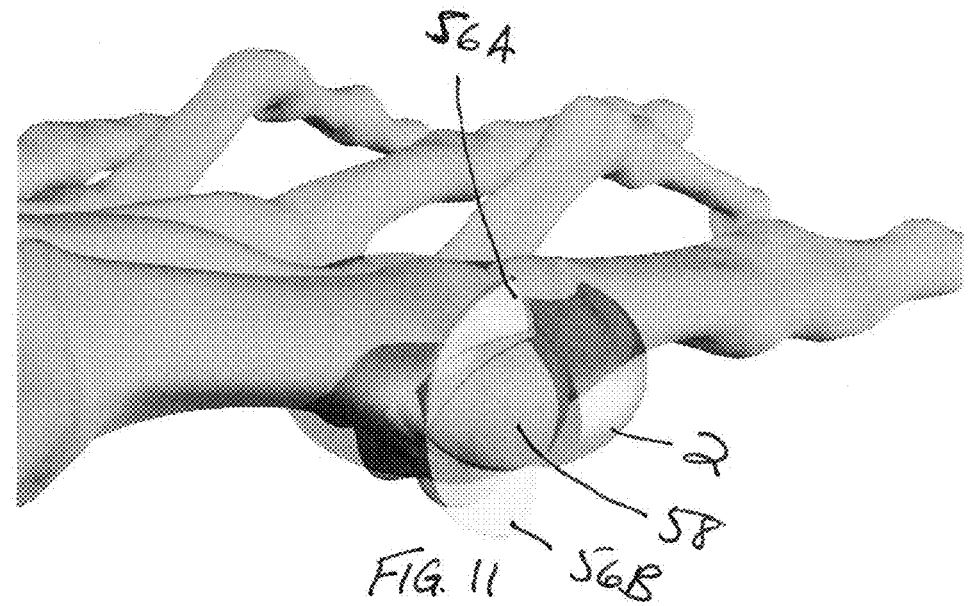
FIG. 11 is a schematic depiction of a foot in which the first MTP capsule has been laid back, according to one embodiment.

In accordance with one embodiment, one method of implanting the capsule anchor 50, bone anchor 54, and the tether 52 as shown in FIG. 9 is set forth as follows. First, an incision is made in the medial side of the first MTP capsule 2. FIG. 10 depicts a schematic representation of the intact first MTP capsule 2. In FIG. 11, an incision has been made in the MTP capsule 2 according to one embodiment, resulting in a portion of the capsule being laid back to create flaps 56A, 56B, and to expose the eminence 58 on the medial side of the first MTP joint.

Figure 12:
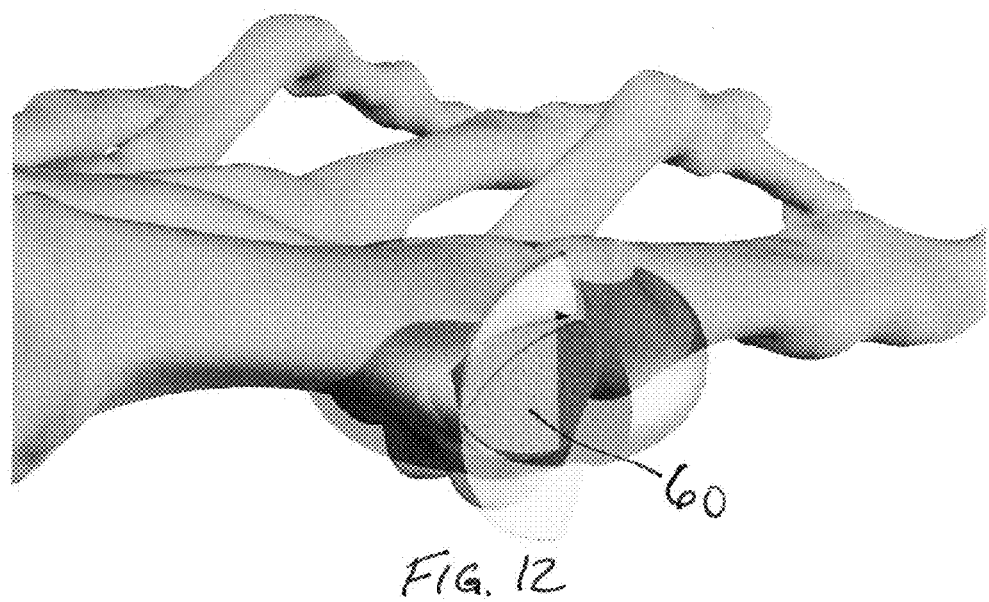
FIG. 12 is a schematic depiction of the foot of FIG. 11, in which the eminence has been removed, according to one embodiment.
Figure 13:
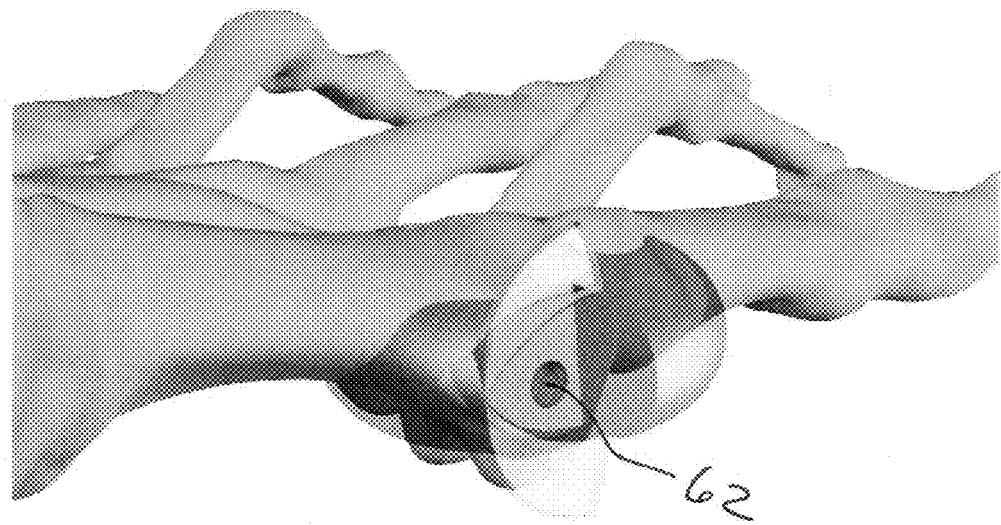
FIG. 13 is a schematic depiction of the foot of FIG. 12, in which a hole has been formed through the first metatarsal bone, according to one embodiment.

Once the eminence 58 is exposed as shown in FIG. 11, a portion or all of the eminence is removed by conventional methods, thereby resulting in a cut surface 60 as shown in FIG. 12 where the eminence had been. As further shown in FIG. 13, once the eminence is removed, a hole 62 is drilled in the metatarsal bone, according to one implementation. Although not depicted in FIG. 13, this hole 62 is drilled all the way through the metatarsal bone.

Figure 14:
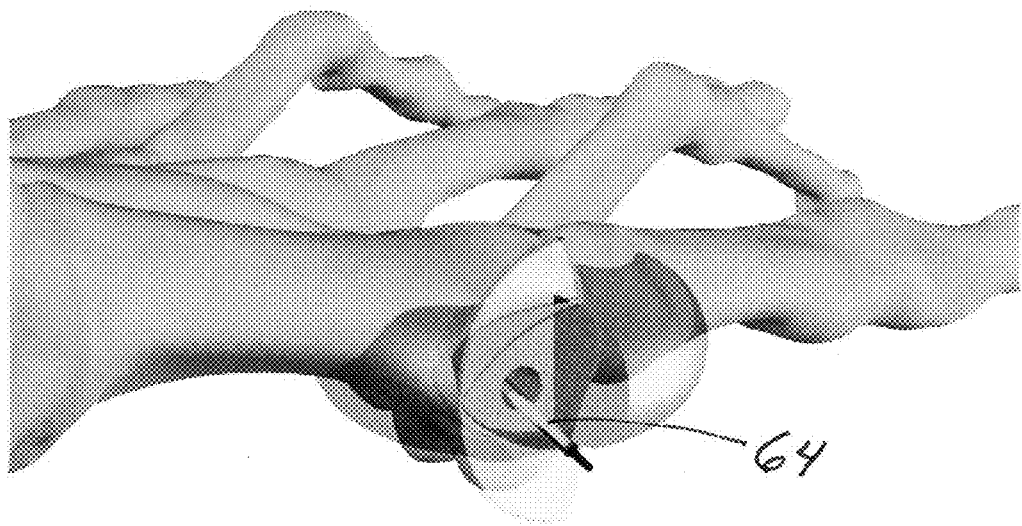
FIG. 14 is a schematic depiction of the foot of FIG. 13, in which an application device has been positioned within the hole, according to one embodiment.
Figure 15:
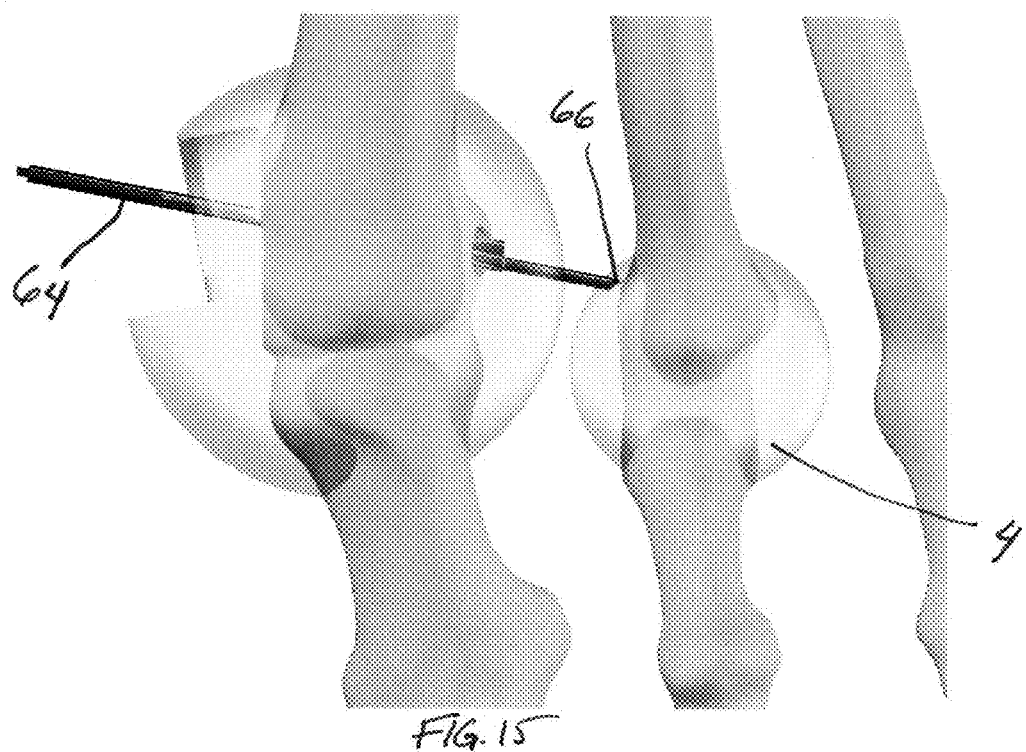
FIG. 15 is a schematic depiction of the foot of FIG. 14, in which the distal end of the application device has been inserted into the second MTP capsule, according to one embodiment.
Figure 16:
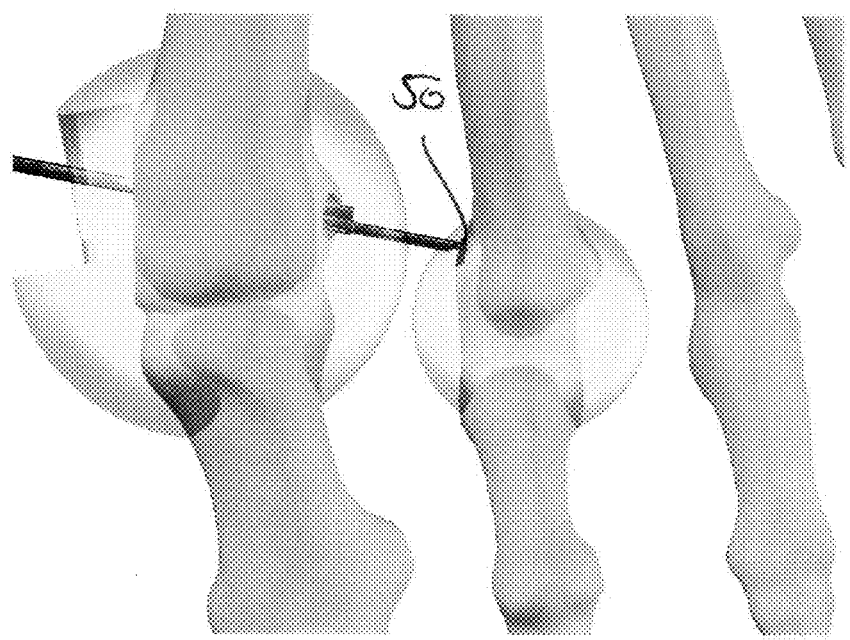
FIG. 16 is a schematic depiction of the foot of FIG. 15, in which an anchor has been deployed from the application device, according to one embodiment.
Figure 17:
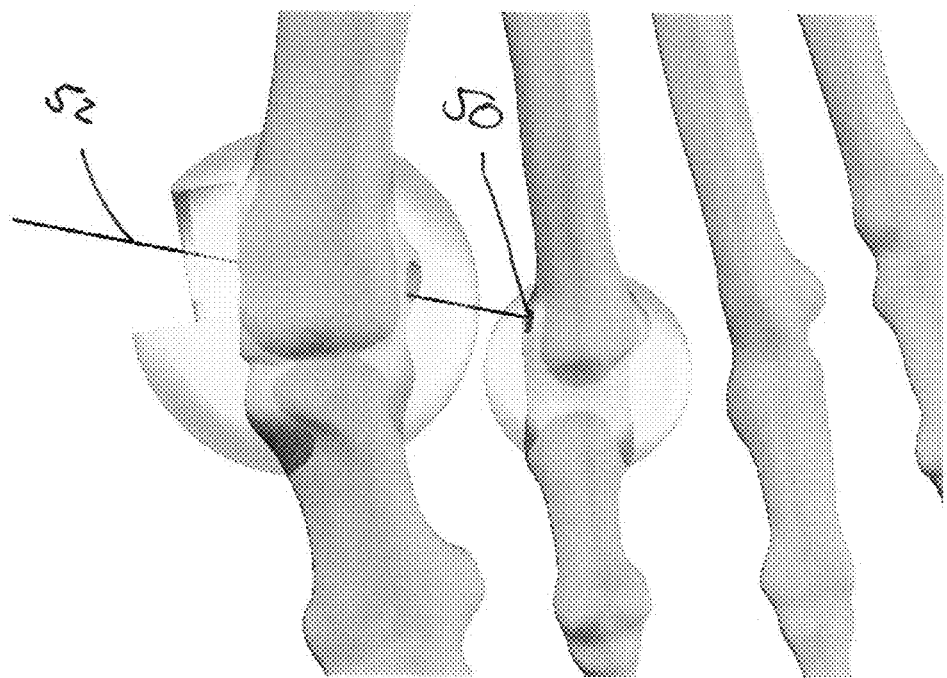
FIG. 17 is a schematic depiction of the foot of FIG. 16, in which the application device has been removed and the treatment device remains, according to one embodiment.

In one implementation as shown in FIG. 14, once the hole 62 is drilled, an application device 64 can be inserted into the hole 62. According to one embodiment, this application device 64 is substantially similar to the application device described above and depicted in FIG. 4, except that the application device 64 contains only one capsule anchor. As shown in FIG. 15, the application device 64 is inserted through the hole 62 in the first metatarsal bone, and the distal tip 66 is inserted into the second MTP capsule. Once the distal tip 66 is positioned as desired, the capsule anchor 50 can be deployed from the distal tip 66 as best shown in FIG. 16. After deployment, the application device 64 can be removed, leaving the anchor 50 in place. FIG. 17 depicts one embodiment in which the implanted capsule anchor 50 and the tether 52 coupled to the anchor 50 after the application device has been removed.

Figure 18:
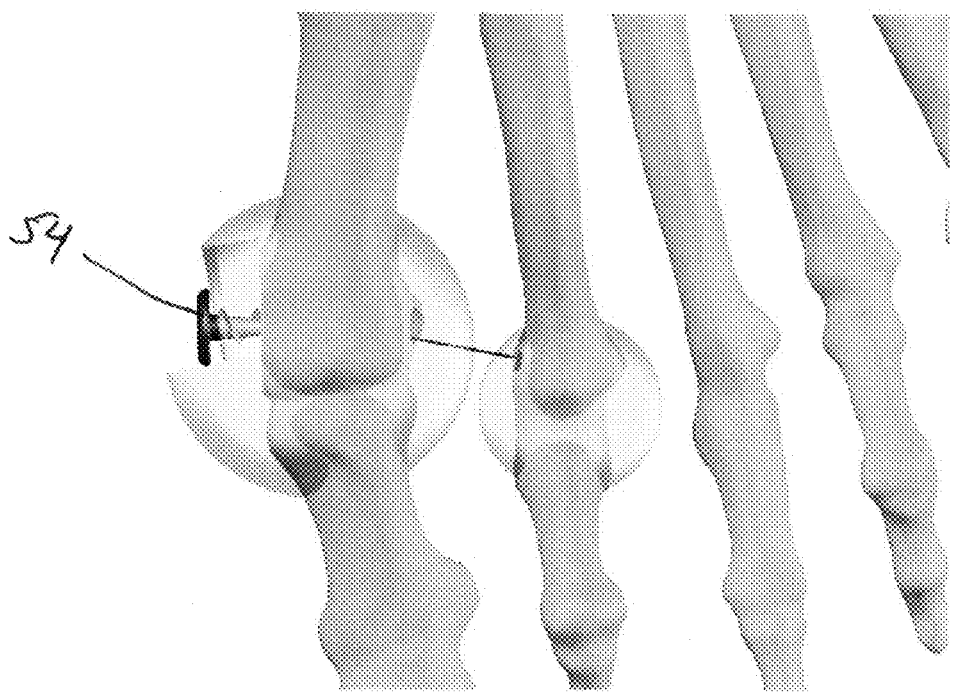
FIG. 18 is a schematic depiction of the foot of FIG. 17, in which a bone anchor is positioned in the hole in the first metatarsal bone, according to one embodiment.

As set forth in one exemplary embodiment in FIG. 18, after the application device has been removed, the bone anchor 54 can be placed in the first metatarsal bone. That is, the bone anchor 54 is inserted or otherwise urged into the hole 62 in the first metatarsal bone. In this embodiment, the anchor 54 has threads and is screwed into the hole 62 on the medial side of the first metatarsal bone. The tether 52 is coupled to the bone anchor 54 such that the tether 52 is tensioned, thereby urging the capsule anchor 50 and the bone anchor 54 together, which, in turn, urges the first metatarsal toward the second metatarsal, thereby treating the bone deformity.

Figure 19A:
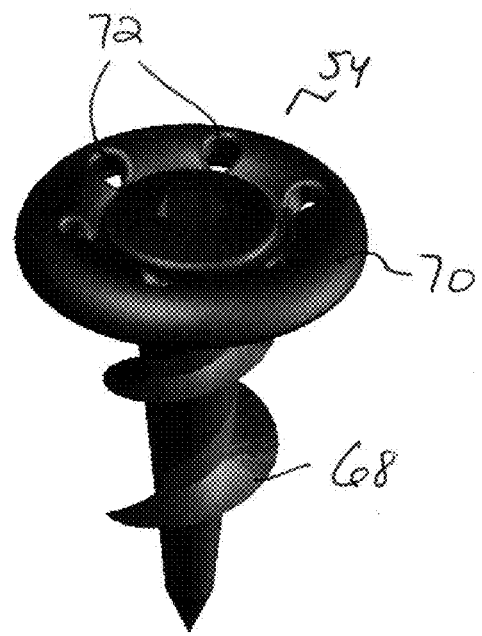
FIG. 19A is a perspective view of a bone anchor, according to one embodiment.
Figure 19B:
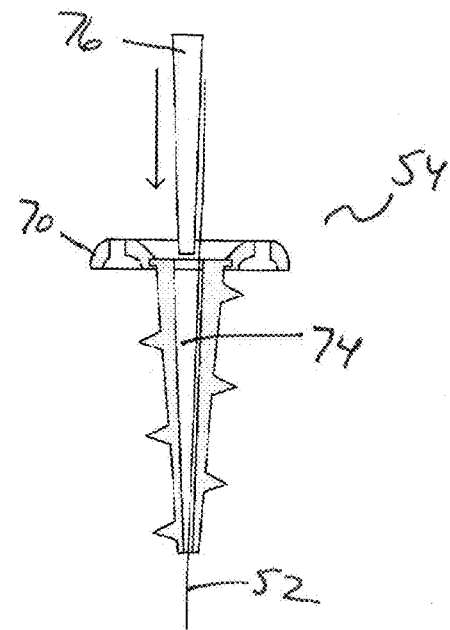
FIG. 19B is a cross-sectional view of the bone anchor of FIG. 19A, according to one embodiment.

In one embodiment as shown in FIGS. 19A and 19B, the bone anchor 54 is a threaded device 54. That is, the device 54 has threads 68 that can be engaged with the inner surface of a drilled hole in any bone such as that shown in FIG. 18. In addition, the bone anchor 54 can also have a head portion 70 with at least one aperture 72 defined within that head portion 70 and a lumen 74 defined through the length of the device 54. According to one embodiment, the tether 52 can be placed through the lumen 74 in the bone anchor 54 and secured in relation to the device 54 with a wedge 76 positioned in the lumen 76 at the head portion 70 as best shown in FIG. 19B. Alternatively, the tether 52 can be secured to the bone anchor 54 by other known means. In a further alternative, the various bone anchor embodiments disclosed and contemplated herein can be any component or device configured to be attachable to bone.

It is understood that any of the bone anchor embodiments contemplated herein can be made of any known material for implantable medical components or devices. In one embodiment, the anchors can be made of a relatively rigid material such as stainless steel, titanium, a rigid polymer such as PEEK, or the like.

Once the bone anchor 54 is placed as shown in FIG. 18 and screwed into the first metatarsal bone or otherwise attached thereto, the resulting capsule anchor, bone anchor, and tether can be placed as best shown in FIG. 9. In accordance with one alternative embodiment, the open medial capsule of FIG. 9 can be closed using the bone anchor 54 and some additional sutures as described below in FIGS. 21-26.

Figure 20:
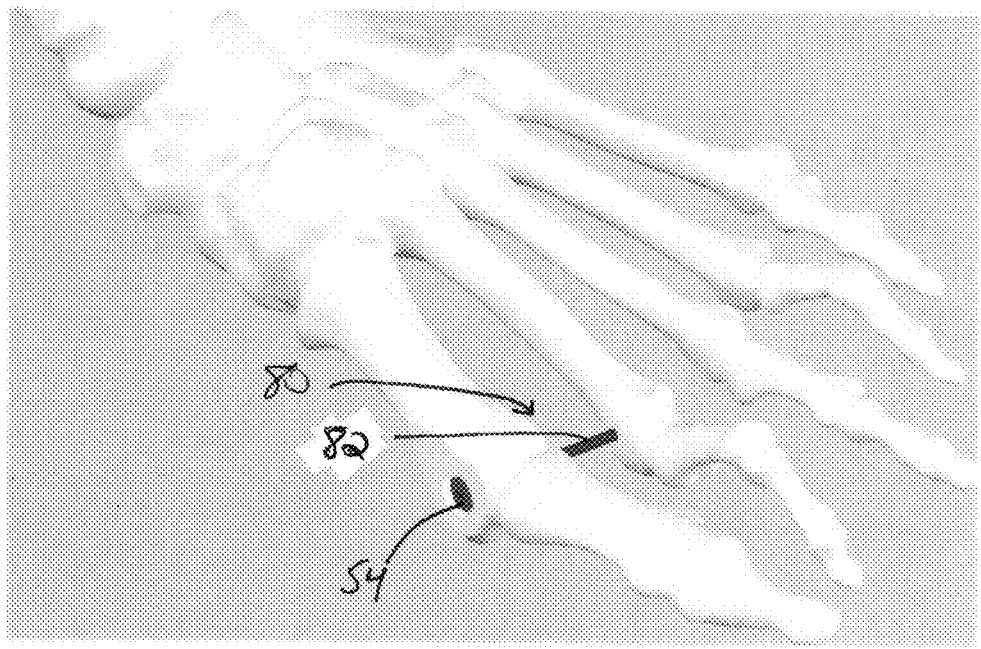
FIG. 20 is a schematic depiction of another implementation of an implantable bone deformity treatment device in a foot exhibiting hallux valgus, according to one embodiment.

Alternatively, the bone anchor 54 can also be used with another bone anchor, instead of an MTP capsule anchor. One example, according to one embodiment as shown in FIG. 20, relates to a treatment device 80 having the bone anchor 54 anchored in the first metatarsal, a second bone anchor (not shown) anchored in the second metatarsal, and a tensioned tether 82 attached to both bone anchors.

Figure 21:
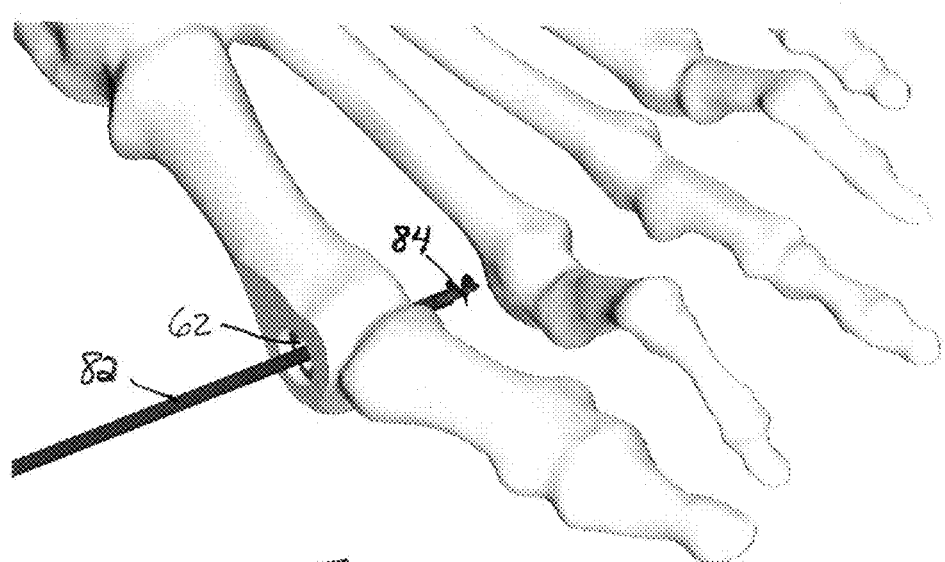
FIG. 21 is a schematic depiction of a foot in which a tether has been positioned within a hole in the first metatarsal bone, according to one embodiment.

According to one embodiment, the treatment device 80 can be implanted using a procedure similar to that depicted in FIGS. 10-18. More specifically, as shown in FIG. 21, a hole 62 such as that shown in FIG. 13 can be formed in the first metatarsal. According to certain implementations, an incision can first be made in the medial side of the first MTP capsule (not shown) and the flaps of the capsule laid back to expose the eminence. The eminence can then be removed and the hole 62 drilled in the cut surface and through the metatarsal. Alternatively, the hole 62 can be formed in any known fashion. Once the hole 62 is formed, the tether 82 is inserted through the hole 62. In one embodiment, the tether 82 can be inserted using an application device such as the device 64 shown in FIGS. 14-16. Alternatively, the tether 82 in this embodiment has sufficient stiffness to be inserted through the hole 62 without an insertion device.

As shown in FIG. 21, one embodiment of the tether 82 includes a bone anchor 84 on the distal end of the tether 82. In this embodiment, the bone anchor 84 has anchoring threads that allow the device 84 to be anchored in the second metatarsal bone. During implantation, the tether 82 is inserted through the hole 62 in the first metatarsal and the distal bone anchor 84 is positioned against the medial side of the second metatarsal bone. According to one embodiment, the bone anchor 84 is anchored in the second metatarsal bone by simply rotating the tether 82 and allowing the anchoring threads of the device 84 to be screwed into the bone. Alternatively, a hole (not shown) can first be formed in the medial side of the second metatarsal by any known method and then the bone anchor 84 can be inserted into the hole.

Figure 22:
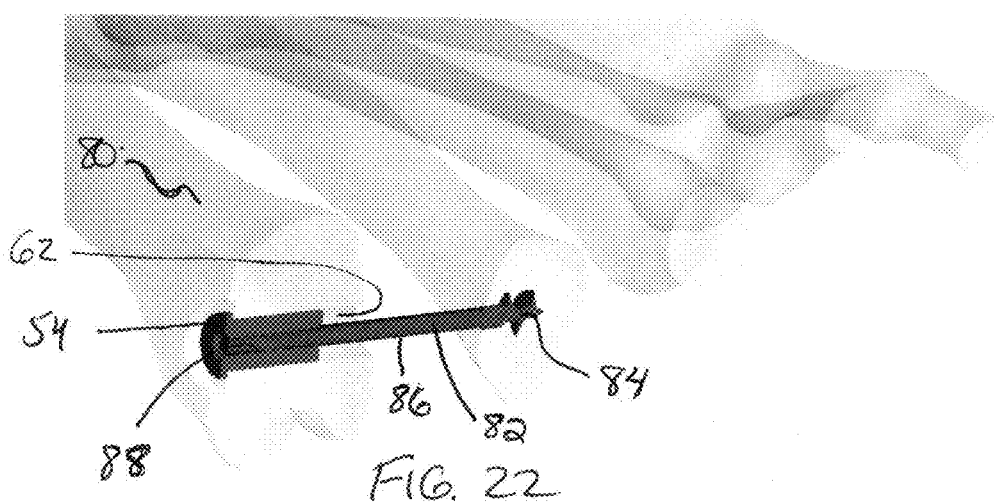
FIG. 22 is a cross-sectional depiction of an implantable bone deformity treatment device, according to one embodiment.

FIG. 22 depicts one embodiment of a treatment device 80 anchored at one end in the second metatarsal bone via the bone anchor 84 and at the other end in the first metatarsal bone via the bone anchor 54. In this embodiment, the tether 82 has threads 86 that mate with the threads 88 in the inner lumen of the bone anchor 54, thereby allowing the tether 82 to be moveably fixed to the bone anchor 54. That is, according to one embodiment, the bone anchor 84 can first be implanted into the second metatarsal bone and then the bone anchor 54 can be inserted into the medial side of the hole 62 and threaded onto the threads 86 of the tether 82.

Alternatively, another embodiment of a treatment device 80 is depicted in FIG. 23. In this embodiment, the tether 82 has teeth 90 (instead of threads) formed along at least one side of the tether 82 that mate with the teeth 92 formed in the inner lumen of the bone anchor 54, thereby providing another mechanism for moveably coupling the tether 82 to the device 54. That is, the bone anchor 84 can be implanted into the second metatarsal bone, and then the bone anchor 54 can be inserted over the tether 82 and into the medial side of the hole 62. According to one implementation, the teeth 90 on the tether 82 and the teeth 90 in the bone anchor 54 can be configured to allow the device 54 to be slid along the tether 82 in a distal direction toward the hole 62 while preventing the device from sliding in a proximal direction.

In an alternative embodiment, the bone anchor that is implanted into the second metatarsal can be a separate bone anchor 100 similar to that depicted in FIGS. 24A and 24B. The device 100 in this embodiment as shown has a head 102 and threads 104 that can be used for insertion into the second metatarsal bone, along with a tether 106 attached to the head 102. In one embodiment, the device 100 and tether 106 can be inserted through a hole in the first metatarsal bone in a similar fashion to that shown in FIGS. 14 and 15. Subsequently, the device 100 can be positioned against the second metatarsal bone and screwed into the bone using a wrench or other similar tool (not shown). Once the bone anchor 100 is implanted into the second metatarsal bone with the tether 106 extending through the hole in the first metatarsal bone, the bone anchor 54 can be inserted over the tether 106 and implanted into the hole in a fashion similar to that depicted in FIG. 18.

Yet another method of treating bone deformation using a bone anchor, according one embodiment, is set forth below. In this embodiment, a bone anchor similar to that depicted in FIGS. 19A and 19B can be used without any other devices. For example, a procedure as described in FIGS. 25-30 can be used to remove the eminence on the medial side of the first metatarsal bone, place a bone anchor into the resulting cut surface, close the first MTP capsule, and tighten the surrounding skin using sutures coupled to the bone anchor. In further alternative implementations, the bone anchor and the procedure as described in FIGS. 25-30 can be used in combination with a capsule anchor and tether as best shown in FIG. 18.

Figure 25:
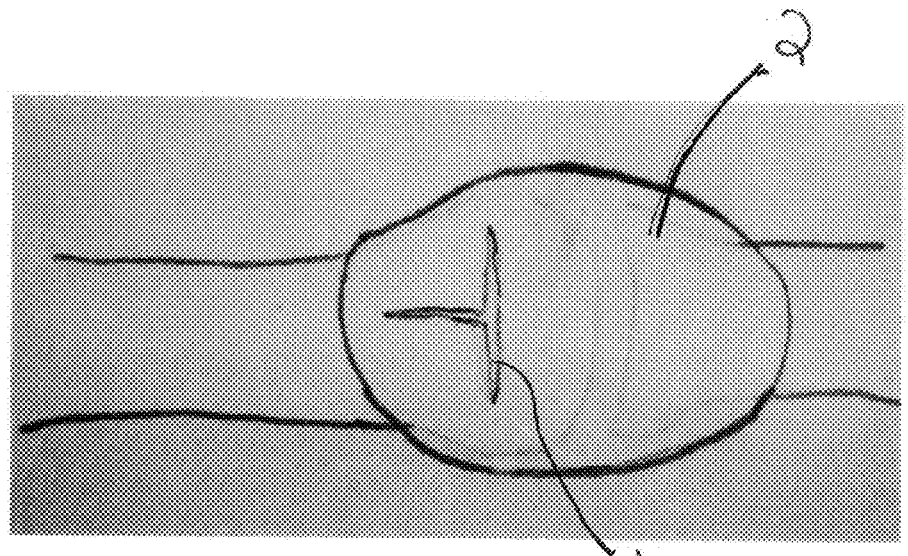
FIG. 25 is a schematic depiction of an MTP capsule with incisions, according to one embodiment.
Figure 26A:
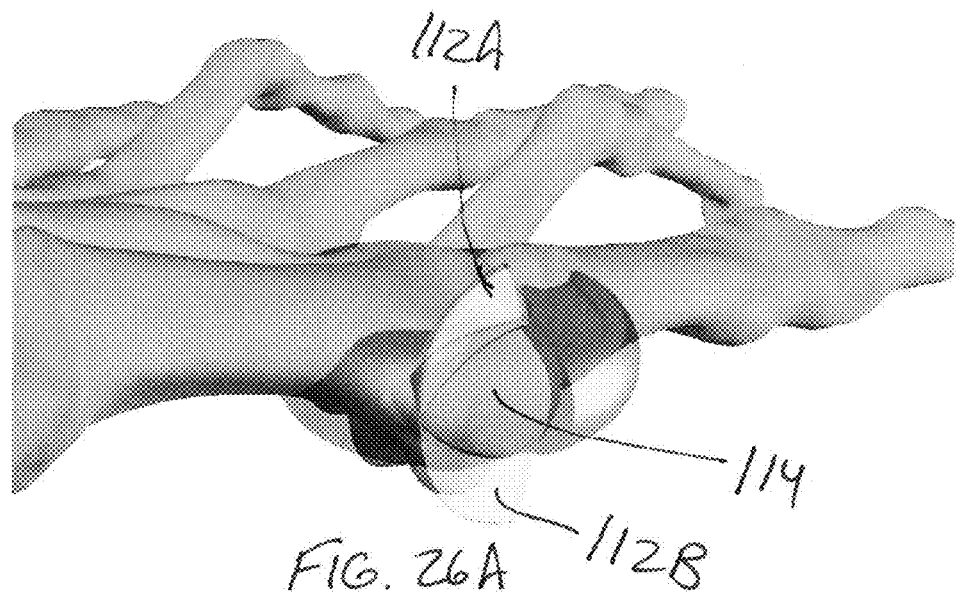
FIG. 26A is a schematic depiction of the MTP capsule of FIG. 25, in which capsule tissue has been laid back, according to one embodiment.
Figure 26B:
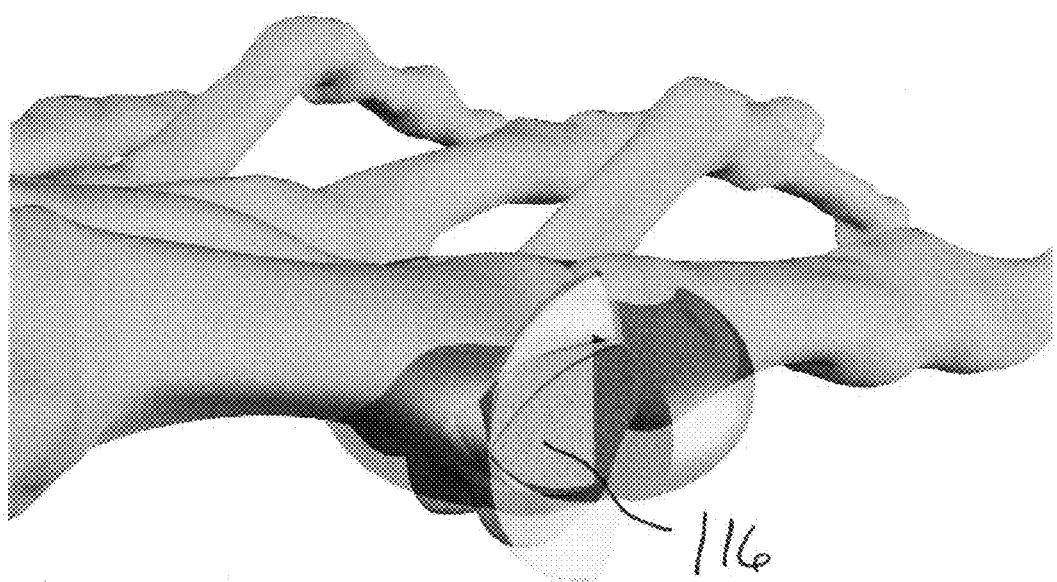
FIG. 26B is a schematic depiction of the MTP capsule of FIG. 26A, in which the eminence has been removed, according to one embodiment.
Figure 27:
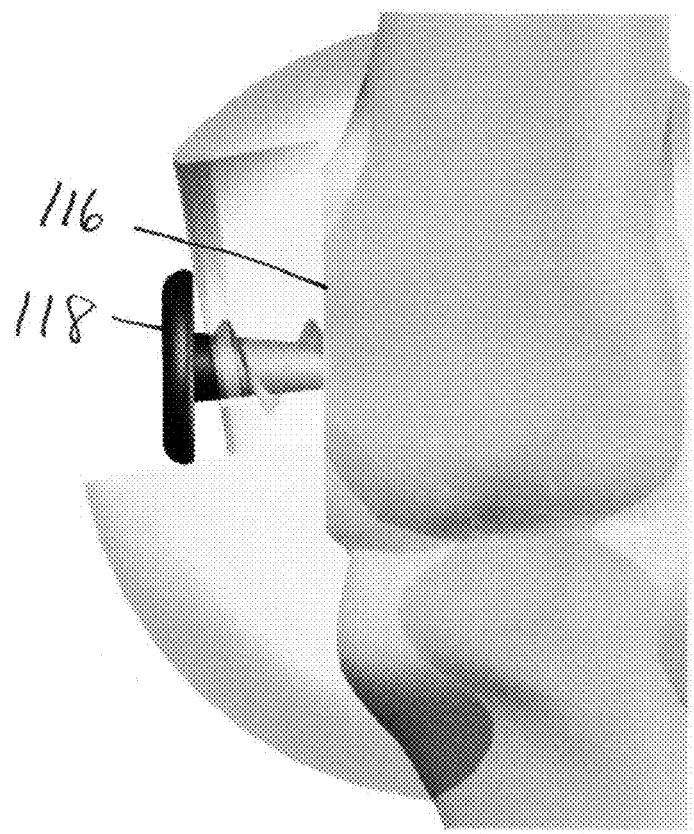
FIG. 27 is a schematic depiction of a bone anchor being positioned in the first metatarsal bone with the MTP capsule of FIG. 26B, according to one embodiment.

A first step in such a procedure in accordance with one implementation is depicted in FIG. 25, where two incisions 110 have been made in the medial side of the first MTP capsule 2. After the incisions have been made, portions of the MTP capsule 2 can be pulled back as shown in FIG. 26A. This results in flaps 112A, 112B being laid back to expose the eminence 114. Once the eminence 114 is exposed, in one embodiment that eminence 114 can be removed to leave a cut surface 116 as shown in FIG. 26B. Upon removal of the eminence 114, a bone anchor 118 according to one implementation can be inserted into the first metatarsal bone as shown in FIG. 27. In one embodiment, a hole (not shown) is first drilled into the first metatarsal bone. Alternatively, the bone anchor 118 is simply screwed or otherwise inserted directly into the bone.

Figure 28:
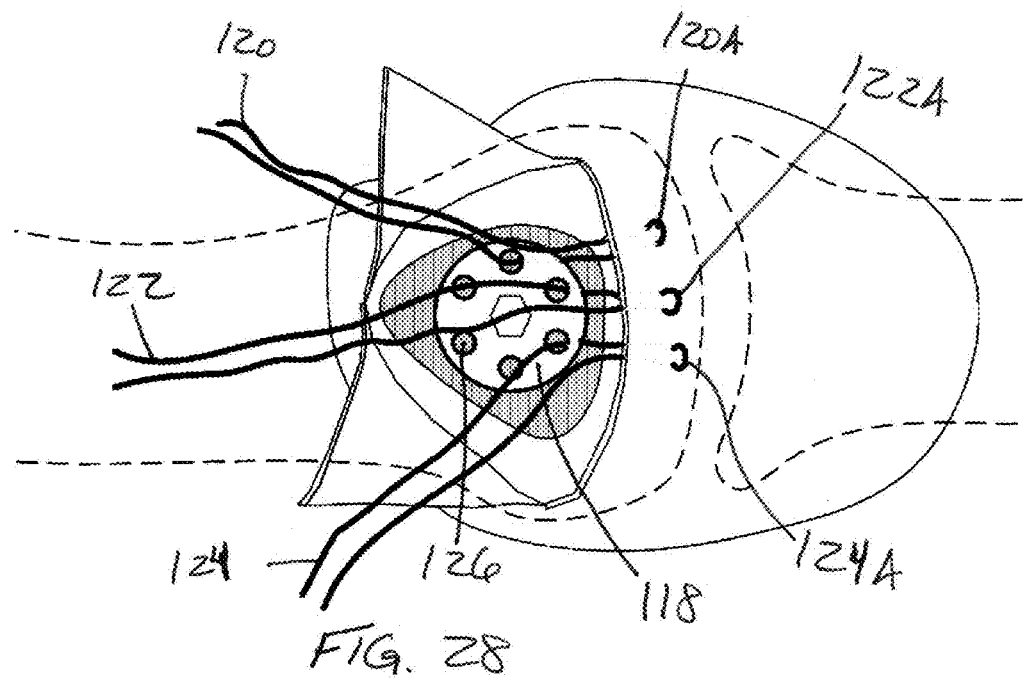
FIG. 28 is a schematic depiction of the bone anchor being positioned within the MTP capsule of FIG. 27, according to one embodiment.
Figure 29:
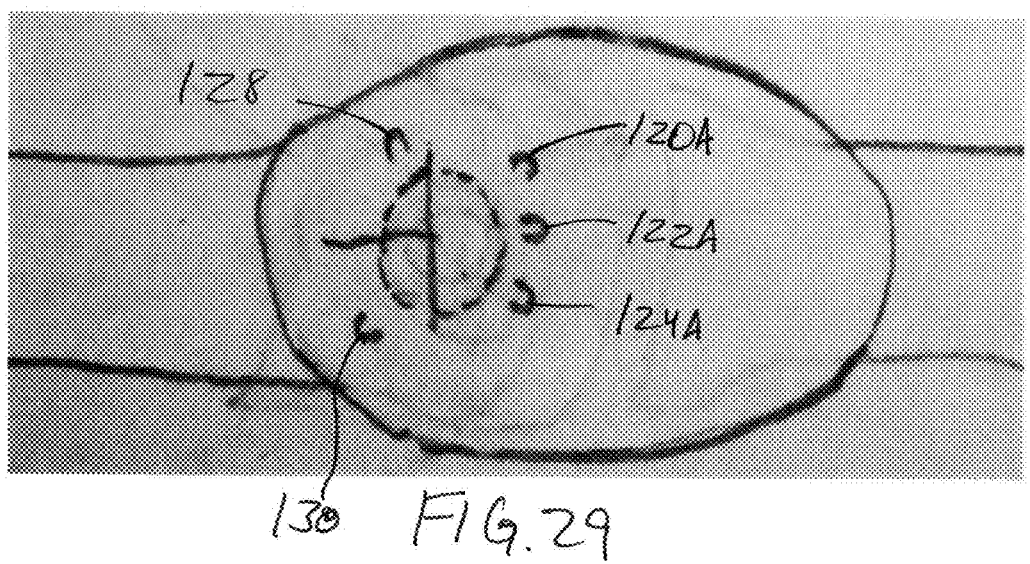
FIG. 29 is a schematic depiction of the tissue of the MTP capsule of FIG. 28 being positioned over the bone anchor, according to one embodiment.
Figure 30:
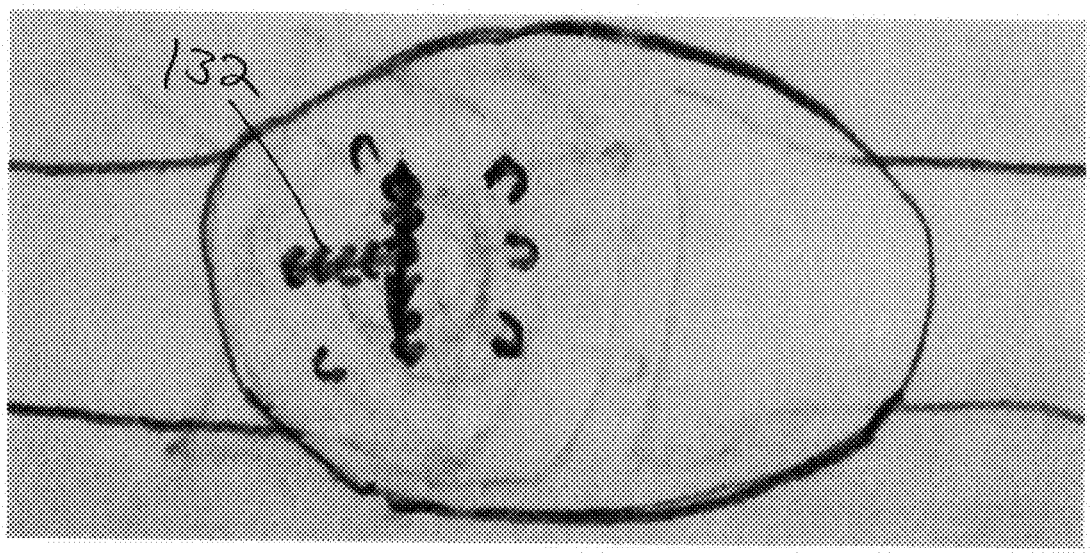
FIG. 30 is a schematic depiction of the incisions of the tissue of the MTP capsule of FIG. 29 being sewn shut, according to one embodiment.

Once the bone anchor 118 is in place, sutures are used to attach to the flaps of tissue or skin around the bone anchor as best shown in FIG. 28. In this figure, three separate sutures 120, 122, 124 have been positioned each through a separate hole 126 in the bone anchor 118 and inserted through a portion of the skin or capsule at points 120A, 122A, 124A. In addition, each of the sutures 120, 122, 124 has been looped at the insertion points 120A, 122A, 124A and extended back to the bone anchor 118. In addition, similar loops are formed as two of these sutures or two additional sutures are inserted through portions of flaps 112A, 112B as well. Once the loops are formed with the sutures 120, 122, 124 inserted through the bone anchor 118, all the sutures are pulled tight to pull the capsule and skin over the bone anchor as best shown in FIG. 29. Once the tissue as been pulled tight as shown, all that is visible are the individual loops 120A, 122A, 124A, 128, 130. In accordance with one implementation, any redundant capsular tissue that remains after the tightening step can be removed. Finally, in one embodiment, the cut tissue edges of the capsule 2 can also be sewn shut as shown in FIG. 30, which depicts the loops 132 of the sutures used to sew the edges together.

Although the present invention has been described with reference to preferred embodiments, persons skilled in the art will recognize that changes may be made in form and detail without departing from the spirit and scope of the invention.

What is claimed is:

1. A method of treating a foot having hallux valgus, comprising:
    positioning a first capsule anchor in a medial side of a metatarsophalangeal ("MTP") joint capsule of the second toe of the foot, wherein the first capsule anchor is coupled to a first end of a first tether;
    positioning a second capsule anchor in a lateral side of a MTP joint capsule of the great toe of the foot, wherein the second capsule anchor is coupled to a second end of the first tether; and
    urging the second capsule anchor toward the first capsule anchor,
    wherein positioning the first capsule anchor comprises:
        inserting a sharp distal tip of an application device into the medial side of the MTP joint capsule of the second toe of the foot, the application device comprising an elongate body comprising a lumen disposed therethrough; and
        urging an advancement rod disposed within the lumen of the application device from a proximal position to a distal position, thereby urging the first capsule anchor out of the lumen through an opening defined in the sharp distal tip and into an appropriate position in relation to the MTP joint capsule of the second toe of the foot.

2. The method of claim 1, wherein positioning the second capsule anchor comprises:
    inserting the sharp distal tip of the application device into the lateral side of the MTP joint capsule of the great toe of the foot; and
    urging the advancement rod from the proximal position to the distal position, thereby urging the second capsule anchor out of the lumen through the opening defined in the sharp distal tip and into an appropriate position in relation to the MTP joint capsule of the great toe of the foot.

* * * * *